(12) United States Patent
Gebert et al.

(10) Patent No.: US 11,213,055 B2
(45) Date of Patent: Jan. 4, 2022

(54) FERMENTATE COMPOSITIONS AND METHODS OF MAKING AND USING THE SAME

(71) Applicant: Third Wave Bioactives, LLC, Wauwatosa, WI (US)

(72) Inventors: Shelly Gebert, Brookfield, WI (US); Matthew Hundt, Bookfield, WI (US)

(73) Assignee: Third Wave Bioactives, LLC, Wauwatosa, WI (US)

( * ) Notice: Subject to any disclaimer, the term of this patent is extended or adjusted under 35 U.S.C. 154(b) by 0 days.

(21) Appl. No.: 16/769,788

(22) PCT Filed: Dec. 27, 2018

(86) PCT No.: PCT/US2018/067651
§ 371 (c)(1),
(2) Date: Jun. 4, 2020

(87) PCT Pub. No.: WO2019/133695
PCT Pub. Date: Jul. 4, 2019

(65) Prior Publication Data
US 2021/0177016 A1    Jun. 17, 2021

Related U.S. Application Data
(60) Provisional application No. 62/611,366, filed on Dec. 28, 2017.

(51) Int. Cl.
*A61K 35/747* (2015.01)
*A23L 3/3463* (2006.01)
(Continued)

(52) U.S. Cl.
CPC ........... *A23L 3/3463* (2013.01); *A01N 63/20* (2020.01); *A23L 3/3499* (2013.01); *A23L 3/3508* (2013.01); *C12P 7/24* (2013.01)

(58) Field of Classification Search
CPC ......... A23L 3/3499; A23L 3/3508; C12P 7/24
(Continued)

(56) References Cited

U.S. PATENT DOCUMENTS

| | | | | |
|---|---|---|---|---|
| 5,849,289 A | * | 12/1998 | Dobrogosz | C07D 319/06 424/93.45 |
| 9,961,914 B2 | | 5/2018 | Sliekers et al. | |

(Continued)

FOREIGN PATENT DOCUMENTS

EP    1192867 A2  *  4/2002  ............... A23B 7/10

OTHER PUBLICATIONS

Arskold et al., "Phosphoketolase pathway dominates in Lactobacillus reuteri ATCC 55730 containing dual pathways for glycolosis", Jouran of Bacteriology, 2008, vol. 190, issue 1, pp. 206-212, retrieved from the Internet. DOI: 10.1128/JB.01227-07.
(Continued)

*Primary Examiner* — Brent T O'Hern
(74) *Attorney, Agent, or Firm* — Andrus Intellectual Property Law, LLP

(57) ABSTRACT

The present inventors disclose new fermentate compositions that display antimicrobial activity against a variety of microorganisms in foods. The fermentate compositions may not only be active at acidic pHs, but also retain antimicrobial activity at elevated pHs including neutral pHs. In addition to new fermentate compositions, the present invention also relates to improved methods for making such fermentate compositions and using unpurified fermentate compositions to effectively preserve food products.

13 Claims, 11 Drawing Sheets

(51) Int. Cl.
*A01N 63/20* (2020.01)
*A23L 3/3499* (2006.01)
*A23L 3/3508* (2006.01)
*C12P 7/24* (2006.01)

(58) Field of Classification Search
USPC .......................................................... 426/335
See application file for complete search history.

(56) References Cited

U.S. PATENT DOCUMENTS

| | | |
|---|---|---|
| 10,040,833 B2 | 8/2018 | Sliekers et al. |
| 10,765,131 B2 | 9/2020 | Dierdorp-Andreae et al. |
| 2007/0172547 A1 | 7/2007 | Kume et al. |
| 2009/0304656 A1 | 12/2009 | Roos |

OTHER PUBLICATIONS

Luthi-Peng et al., "Production and stability of 3-hydroxpropionaldehyde in Lactobacillus reuteri", Applied Microbiology and Biotechnology, 2002, vol. 60, issue 1-2, pp. 73-80, retrieved from the Internet. DOI: 10.1007/s00253-002-1099-0.

Talarico et al., "Chemical characterization of an antimicrobial substance produced by Lactobacillus-reuteri", Antimicrobial Agents and Chemotherapy, 1989, vol. 33, issue 5, pp. 674-679, retrieved from the Internet. DOI: 10.1128/AAC.33.5.674.

Talarico et al., "Production and isolation of reuterin, a growth inhibitor produced by Lactobacillus reuteri", Antimicrobial Agents and Chemotherapy, 1988, vol. 32, issue 12, pp. 1854-1858, retrieved from the Internet. DOI: 10.1128/AAC.32.12.1854.

International Search Report and Written Opinion in corresponding International Application No. PCT/US2018/067621 dated Mar. 21, 2019.

* cited by examiner

FERMENTATE COMPOSITIONS AND METHODS OF MAKING AND USING THE SAME

CROSS-REFERENCE TO RELATED PATENT APPLICATIONS

The present application claims the benefit of priority to United States Provisional Patent Application No. 62/611,366, filed on Dec. 28, 2017, the content of which is incorporated herein by reference in its entirety.

BACKGROUND

The Background and Summary are provided to introduce a foundation and selection of concepts that are further described below in the Detailed Description. The Background and Summary are not intended to identify key or essential features of the claimed subject matter, nor are they intended to be used as an aid in limiting the scope of the claimed subject matter.

Food fermentates on the market today are typically made from of Propionibacteria and Lactic Acid Bacteria (LAB) such as *Lactobacillus, Lactococcus*, and *Staphylococcus*. During fermentation, these bacteria can produce varying levels of organic acids, peptides as well as other biologically active compounds. At the end of fermentation, the resulting liquid is spray dried into a powder. This powder, when incorporated in a food matrix at an appropriate dosage, can provide an improved shelf-life in foods that are commonly spoiled when processed without a preservative. Currently, fermentates that may be applied to foods can contain a range of organic acids (including propionic, lactic, and acetic, among others). These organic acids help inhibit the growth of bacteria, yeast, and molds by disrupting their cellular function, primarily by forcing the microbes to exert energy on balancing $H^+$ concentration across their outer membranes, as opposed to growing and increasing their abundance in food. This metabolic shift leads to a reduction in microbial outgrowth and an extension in food quality post-production.

Because the efficacy of organic acids is linked to their $pK_a$'s, these organic acids are more effective in lower pH foods (pH<5.5). This limitation forces food manufacturers to acidify foods further than they would prefer or makes the use of organic acid-based products in more neutral or higher pH food impractical (pH>5.5). Furthermore, some microorganisms are inherently resistant to organic acids and the low pH of the food matrix (Palma et al. BMC Genomics (2015) 16:1070). Given these limitations of organic acids, as well as the inherent resistance of some microorganisms to organic acids in general, there remains a need in the art for new fermentates that may be applied to foods to control resistant microorganisms, as well as new fermentates that function independently of pH.

SUMMARY

In one aspect of the present invention, fermentates are provided. The fermentates may include a cellular mass component from a fermenting microorganism. Optionally, the fermentates may include reuterin (β-hydroxypropionaldehyde).

In another aspect, the present invention relates to methods for producing a fermentate having antimicrobial activity. The methods may include (a) making or obtaining a first liquid composition having a pH between 3 and 8, the first liquid composition may include a fermentable carbohydrate, *Lactobacillus reuteri*, water, and a growth media capable of supporting the growth of the *Lactobacillus reuteri*; (h) incubating the first liquid composition under anaerobic conditions at a temperature for a first time period to produce a second liquid composition having a pH; (c) adding glycerol and/or a base to the second liquid composition; and (d) incubating the second liquid composition under anaerobic conditions at the temperature for a second time period to produce a first fermentate.

In a further aspect of the present invention, food products are provided. The food products may include anyone of the fermentates disclosed herein.

In a still further aspect, methods for killing or inhibiting the growth of a contaminating microorganism on a food product are provided. The methods may include making or obtaining any one of the fermentates disclosed herein; and applying an effective amount of the fermentate to at least one surface of the food product so as to kill or inhibit the growth of the contaminating microorganism on the food product.

Various other features, objects and advantages of the disclosure will be made apparent from the following description taken together with the drawing.

DETAILED DESCRIPTION

Figure 1:
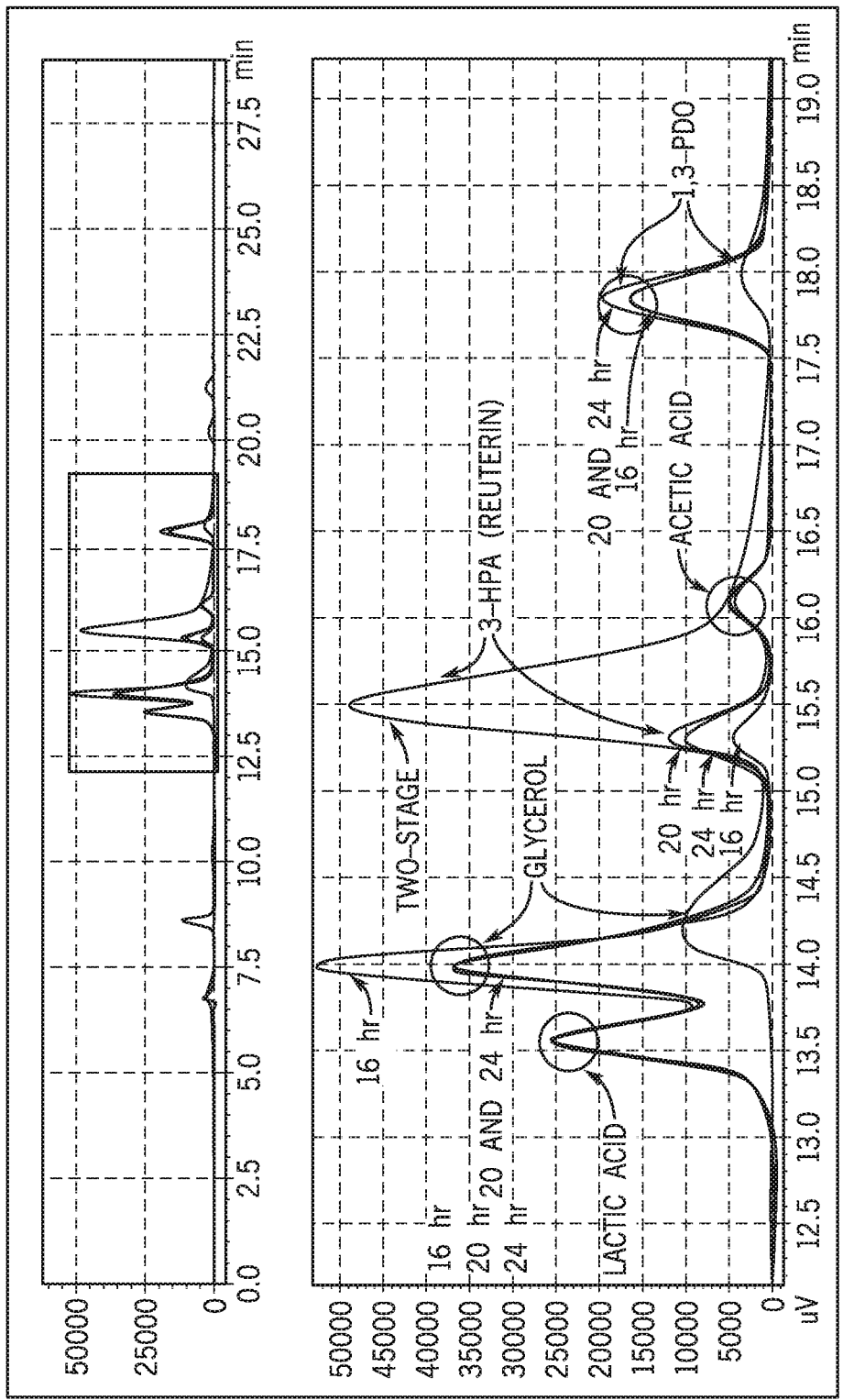
FIG. 1 shows an HPLC profile comparing the production of an *L. reuteri* by-product that uses a two-stage process to obtain a relatively pure form of reuterin vs the single stage fermentation and non-purified version developed by the inventors at various time points in fermentation (16 hr, 20 hr, and 24 hr). The circles highlight areas where un-purified by-products are present.

Here, in the non-limiting Examples, the present inventors have developed new fermentate compositions that may be applied to foods that display antimicrobial activity against a variety of microorganisms that are substantially unaffected by known fermentate compositions. The fermentate compositions disclosed herein are not only active at acidic pHs, but also retain antimicrobial activity at elevated pHs including neutral pHs. The disclosed fermentate compositions will allow food manufacturers to increase the pH of the foods that they are producing to improve sensory aspects (i.e., flavor) and are effective in preventing food contamination by microbial species resistant to other known fermentates.

In some embodiments, the present inventors further disclose that the new fermentate compositions may include salts of lactate such as, without limitation, sodium lactate, calcium lactate, potassium lactate, or ammonium lactate.

In addition to new fermentate compositions, the present invention also relates to improved methods for making such fermentate compositions. The present inventors demonstrate, in part, that the timing of glycerol addition to the fermentation mixture as well as the temperature of the fermentation used to produce the disclosed fermentates significantly improve the antimicrobial activity of the fermentates.

Fermentate Compositions

In one aspect of the present invention, fermentates are provided. As used herein, a "fermentate" refers to a complex mixture produced by a fermentation process that may include a cellular mass component from a microorganism, unspent media components, and metabolites (i.e., unused substrates and/or fermentation end-products). In some embodiments, the fermentates may include a cellular mass component from a fermenting microorganism.

In some embodiments, the fermentates may include reuterin ($\beta$-hydroxypropionaldehyde). Reuterin is an antimicrobial substance produced as an intermediate metabolite during the anaerobic fermentation of glycerol by some microorganisms such as Lactobacillus reuteri. See, e.g., El-Ziney et al., Biotechnology Letters, 20(10): 913-916 (1998) ("El-Ziney 1998"); Talarico et al., Antimicrobial Agents and Chemotherapy, 32(12) 1854-1858 (1988) ("Talarico 1988"). In Lactobacillus reuteri for example, the anaerobic fermentation of glycerol occurs in two steps. In the first step, the enzyme glycerol dehydratase converts glycerol to reuterin. In the second step, reuterin undergoes an aldehydic dismutation by glycerol oxidoreductase to form 1,3 propanediol (1,3 PPD) (aka trimethylene glycol (TMG)) and $\beta$-hydroxypropionic acid ($\beta$-HPA).

As used herein, "reuterin" may refer to the chemical $\beta$-hydroxypropionaidehyde (or 3-hydroxypropanal) in the various forms that this chemical may be found. For example, the reuterin may, without limitation, be in hydrate form, aldehyde form, or dimer form.

The disclosed fermentates may be produced using one or two stages using, for example, Lactobacillus reuteri as the fermenting microorganism. In a two-stage method, two separate anaerobic fermentations are carried out. See, e.g., Talarico 1988; U.S. Pat. No. 5,849,289 to Dobrogosz et al. In the first fermentation, Lactobacillus reuteri is mixed with a fermentable carbohydrate such as glucose under anaerobic conditions to allow the growth of the Lactobacillus reuteri cells and the concomitant increase in cellular mass. During this first fermentation, glucose may be converted to ethanol, lactic acid, and/or lactate. Following the first fermentation, the Lactobacillus reuteri cells are separated from the spent media of the first fermentation and resuspended in water and glycerol. In the second fermentation, the Lactobacillus reuteri cells are incubated with glycerol under anaerobic conditions to produce reuterin and other end products such as 1,3 PPD and $\beta$-HPA. Following the second fermentation, the produced reuterin may be purified using methods known in the art or the unpurified product of the second fermentation may be used in downstream applications such as exemplified in the non-limiting Examples disclosed herein.

In a one-stage method of reuterin production, the anaerobic fermentations of glycerol and a fermentable carbohydrate such as glucose may be carried out in the same media in a single fermentation process. See, e.g., El-Ziney 1998. In such fermentations, the final un-purified fermentates would include reuterin and other glycerol fermentation end-products such as 1,3 PPD and $\beta$-HPA, as well as, glucose fermentation end-products such as ethanol, lactic acid, and/or lactate.

As used herein, a "cellular mass component" refers to any mixture of proteins, lipids (i.e., membranes), carbohydrates, metabolites, etc. from the fermenting microorganism. For example, as a fermenting microorganism grows it produces new cells that generally include additional cellular mass such as, without limitation, cell membranes, nucleic acids (i.e., DNA and/or RNA) internal subcellular structures, and proteins (i.e., membrane-bound, secreted, and/or intracellular).

As used herein, a "fermenting microorganism" refers to a microorganism that can ferment glycerol. Suitable fermenting microorganisms may include, without limitation, several members of the genera Clostridia, Lactobacilli, Klebsiella, or Citrobacter. See, e.g., Dishisha et al., Microbial Cell Factories 13:76 (2014). Suitable fermenting microorganisms from these genera may include, without limitation, Lactobacillus reuteri, Enterobacter agglornerans, Klebsiella pneumoniae, Citrobacter freundii, Aerobacter aerogenes, Clostridium butryicum, Lactobacillus coryinformis, or Lactobacillus collinoides. As used herein, several strains of "Lactobacillus reuteri" capable of fermenting glycerol to, for example, reuterin are known in the art and may include, without limitation, Lactobacillus reuteri 1063, Lactobacillus reuteri 20016, Lactobacillus reuteri 12002, Lactobacillus reuteri INIA P579, Lactobacillus reuteri ATCC 53608, Lactobacillus reuteri ATCC 23272, Lactobacillus reuteri ATCC PTA-6475, Lactobacillus reuteri ATCC 55730, Lactobacillus reuteri. SD2112.

In some embodiments of the disclosed reuterin fermentates, the reuterin may be at a concentration between about 0.01 mM and about 500 mM or any range therein. In some embodiments, the reuterin may be at a concentration between about 5 mM and about 50 mM.

In some embodiments, the fermentates may include reuterin at a purity below 80%, 75%, 70%, 65%, 60%, 55%, 50%, 45%, 40%, 35%, 30%, 25%, 20%, 15%, or 10%. In some embodiments, the fermentates may include reuterin at a purity between about OA % and about 40% or any range therein. In some embodiments, the fermentates may include reuterin at a purity between about 1% and about 20%.

As used herein, the "purity" of a substance in a fermentate may be determined by performing an HPLC analysis of the fermentate and then determining the relative peak heights of the substance to the peak heights of the remaining substances in the fermentate.

In some embodiments, the disclosed fermentates may further include at least one or two metabolites selected from the group consisting of 1,3 propanediol (1,3 PPD) (aka trimethylene glycol (TMG)) and β-hydroxypropionic acid (β-HPA). As discussed above, 1,3 PPD and β-HPA are glycerol fermentation end-products and thus will be present in the fermentates disclosed herein produced by either the two-stage or one-stage production processes. 1,3 PPD may be at a concentration in the disclosed fermentates between about 0.01 mM and about 500 mM or any range therein. In some embodiments, the 1,3 PPD may be at a concentration between about 5 mM and about 100 mM. β-HPA may be at a concentration in the disclosed fermentates between about 0.01 mM and about 500 mM or any range therein. In some embodiments, the β-HPA may be at a concentration between about 5 mM and about 100 mM.

In some embodiments, the disclosed fermentates may further include at least one, two, or three metabolites selected from the group consisting of ethanol, lactate, and lactic acid. As discussed above, ethanol, lactic acid, and/or lactate are fermentation end-products produced by the fermentation of a fermentable carbohydrate such as glucose and thus will be present in the fermentates disclosed herein produced by the one-stage production process. Ethanol may be at a concentration in the disclosed fermentates between about 0.01 mM and about 500 mM or any range therein. Lactic acid may be at a concentration in the disclosed fermentates between about 0.01 mM and about 500 mM or any range therein. Lactate may be at a concentration in the disclosed fermentates between about 0.01 mM and about 500 mM or any range therein.

As demonstrated in the non-limiting Examples, the present inventors show that the disclosed fermentates retain their antimicrobial activity above acidic pHs. Thus, in some embodiments, the fermentates may have a pH between about 1 and about 14, between about 3 and about 12. Suitably, the pH of the fermentate is between about 1 and about 9 or between about 4 and about 9.

In some embodiments, the fermentates may be further processed to be a concentrated liquid or a dry powder. Methods of concentrating fermentates to produce concentrated liquids and/or dry powders are generally known in the art. For example, the present inventors disclose in the non-limiting Examples that the disclosed fermentates may be evaporated using a falling film or similar system or may be spray-dried on a Buchi B-290 spray dryer.

As detailed in the non-limiting Examples, the inventors have observed that different bases (i.e., CaOH. NaOH, KOH, and NH$_3$OH) may be used in *Lactobacillus reuteri* fermentations without significantly negatively affecting the antimicrobial activity of the final fermentates. Surprisingly, the inventors have observed that if calcium hydroxide, sodium hydroxide, potassium hydroxide, or ammonium hydroxide are used to adjust the pH of the fermentate, the resulting calcium lactate, sodium lactate, potassium lactate, or ammonium lactate in the fermentate do not significantly impact the antimicrobial activity of the fermentate. Accordingly, in some embodiments, the fermentates may further include a salt of lactate. Suitable salts of lactate may include, without limitation, calcium lactate, sodium lactate, potassium lactate, or ammonium lactate. The salt of lactate may be at a concentration between about 0.01 mM and about 500 mM, or any range therein, in the fermentates disclosed herein.

Methods for Producing a Fermentate

In another aspect, the present invention relates to methods for producing a fermentate having antimicrobial activity. The methods may include (a) making or obtaining a first liquid composition having a pH between 3 and 8, the first liquid composition may include a fermentable carbohydrate, *Lactobacillus reuteri*, water, and a growth media capable of supporting the growth of the *Lactobacillus reuteri*; (b) incubating the first liquid composition under anaerobic conditions at a temperature for a first time period to produce a second liquid composition having a pH; (c) adding glycerol and/or a base to the second liquid composition; and (d) incubating the second liquid composition under anaerobic conditions at the temperature for a second time period to produce a first fermentate.

In some embodiments, the methods for producing a fermentate having antimicrobial activity may further include evaporating the first fermentate to produce a second fermentate. Methods of evaporating fermentates to produce concentrated liquids are generally known in the art. For example, evaporation step may be performed using a falling film or similar system.

In some embodiments, the methods for producing a fermentate having antimicrobial activity may further include spray-drying the second fermentate to produce a powdered fermentate. Methods of spray-drying fermentates are generally known in the art. For example, the present inventors disclose in the non-limiting Examples that the disclosed fermentates may be spray-dried on a Buchi B-290 spray dryer.

As used herein, a "fermentable carbohydrate" may be any carbohydrate that may support the growth of *Lactobacillus reuteri*. The fermentable carbohydrate may be a monosaccharide or a disaccharide. Suitable fermentable carbohydrates may include, without limitation, dextrose, glucose (L or D forms), sucrose, lactose, or maltose. In some embodiments, the fermentable carbohydrate may be at a concentration between about 10 mM and about 500 mM in the first liquid composition.

Growth media capable of supporting the growth of the *Lactobacillus reuteri* is generally known in the art. For example, modified versions of DeMan, Rogosa, Sharpe (MRS) media are disclosed in El-Ziney 1998. The growth media may also be the media used by the present inventors in the non-limiting Examples. For example, media containing a source of nitrogen, amino acids, vitamins and trace minerals may be used.

The present methods for producing a fermentate having antimicrobial activity may be performed under anaerobic conditions. The anaerobic conditions may be effectuated, without limitation, using Nitrogen gas which may be sparged through the media or set to gas over the headspace of the fermentation vessel.

The pH of the first and/or second liquid compositions of the present methods may be controlled using a "base." As used herein, the "base" may be a base including, without limitation, calcium hydroxide, sodium hydroxide, potassium hydroxide, or ammonium hydroxide.

In some embodiments, the "first time period" may be zero hours. In such embodiments, the glycerol is added immediately to the first/second liquid composition.

Alternatively, in some embodiments, the first liquid composition may lack glycerol. In certain such embodiments, the "first time period" may be between about 9 hours and about 13 hours, about 10 hours and about 12 hours, about 10 hours, about 11 hours, or about 12 hours. In certain such embodiments, the glycerol and/or the base may added to the second liquid composition when the pH of the second liquid composition drops below a pH of 7, 6.5, 6, 5.5, 5, 4.5, 4, 3.5, 3, 2.5, or 2. The glycerol may be added once to the second liquid composition or may be added repeatedly in 2, 3, 4, or more aliquots to give a final glycerol concentration.

In some embodiments, the glycerol may be at a final concentration between about 100 mM and about 400 mM, or any range therein, in the second liquid composition.

The temperature used in the methods for producing a fermentate having antimicrobial activity may be between about 25° C. and about 40° C. The inventors also discovered that lowering the fermentation temperature in the present methods from 37° C. or 35° C. to 30° C. surprisingly improved the antimicrobial activity of one-stage *Lactobacillus reuteri* fermentates. See Examples. Accordingly, in some embodiments, the temperature used in the methods for producing a fermentate having antimicrobial activity may be between about 28° C. and about 32° C. or about 30° C.

In some embodiments, the summation of the first time period and the second time period may be between about 22 hours and about 26 hours, or about 24 hours.

In some embodiments, the pH of the first liquid composition may be about 7, 6, 5.5, 5, 4.5 or 4.0.

Food Products

In a further aspect of the present invention, food products are provided. The food products may include anyone of the fermentates disclosed herein. Surprisingly, as reported in the non-limiting Examples, the present inventors demonstrate that unpurified *Lactobacillus reuteri* fermentates displayed significant antimicrobial activity against various microorganisms and that such antimicrobial activity was pH-independent. Such results are counterintuitive given that it is commonly expected in the art that the reuterin, if present, should be purified from such fermentates prior to application to a food product. See, e.g., El-Ziney et al., *Journal of Food Protection* 62(3) 257-261 (1999) ("El-Ziney 1999"); Montiel et al., *Food Microbiology* 44 1-5 (2014) ("Montiel 2014").

As used herein, a "food product" may include any food product susceptible to microbial contamination or degradation. In some embodiments, the food product may be any food product that has a water activity greater than 0.2, 0.3, 0.35, 0.4, 0.45, 0.5, 0.55, 0.6, 0.65, 0.7, 0.75, 0.8, 0.85, or 0.9. Suitable food products may include, without limitation, culinary items, bakery items, cereals, pasta, meats, dairy items, rice, fish, nuts, beverages, confections, pet food, fruits, and vegetables.

Bakery items may include, without limitation, breads, buns, rolls, quick breads (biscuits, muffins, tortillas, cornbread, etc.), sweet goods (cakes, brownies, cookies, pies, etc.), or bakery fillings (dairy-based, fruit-based, etc.).

Meats may include, without limitation, cured meats, raw beef pork (ground meat, whole muscle, etc.), raw poultry (ground poultry, whole muscle, etc.), fermented meats, emulsified meats (hot dogs, etc.), or dried meats.

Culinary items may include, without limitation, dressings, condiments, mayonnaise, sauces and gravies, soups, ready to eat dips, salsa, spreads, ready to eat side items (coleslaw, potato salad, chicken salad, etc.), ready to eat meals (lasagna, casserole, pasta dishes, etc.), jams, jellies, marmalades, fruit fillings, desserts and puddings, or syrups.

Beverages may include, without limitation, teas, coffee and coffee-based drinks, fruit and vegetable juices, fermented beverages, beverage concentrates, soft drinks, acidified milk drinks and milk-based beverages, carbonated soft drinks, drink mixers (base used for bloody marys, margaritas, cocktails, etc.), beer, or wine.

Confections may include, without limitation, chocolate and chocolate-based confections, cakes, cookies, and other sweet treats.

Dairy items may include, without limitation, fresh fermented dairy (cottage cheese, cream cheese, etc.), dairy-based drinks (yogurt drinks, high-protein dairy drinks, etc.), flavored milks, cheese (shredded cheese, cheese blocks, etc.), whipped toppings, dairy-based desserts (flan, custard, pudding, etc.), dairy-based dips (sour cream-based, Greek yogurt-based, etc.), butter and spreads.

Pet food may include, without limitation, kibble, low- and high-moisture treats, refrigerated rolls (meat rolls, veggie rolls, etc.), palatants and flavor-enhancers, broths, or jerky.

In some embodiments, the food product may have a pH between about 1 and about 14, about 1 and about 10, about 1 and about 9, about 3 and about 8, or about 4 and about 8.

Methods for Inhibiting the Growth of a Microorganism on a Food Product

In a still further aspect, methods for killing or inhibiting the growth of a contaminating microorganism on a food product are provided. The methods may include making or obtaining any one of the fermentates disclosed herein; and applying an effective amount of the fermentate to at least one surface of the food product so as to kill or inhibit the growth of the contaminating microorganism on the food product. In certain embodiments, the step of making or obtaining a fermentate includes making or obtaining a fermentate that includes reuterin (β-hydroxypropionaldehyde). In certain embodiments, the fermentate is a *Lactobacillus reuteri* fermentate. The reuterin may be at a purity between about 0.1% and about 40% in the fermentate.

As used herein, a "contaminating microorganism" may be any microorganism capable of contaminating a food product. The contaminating microorganism may be a yeast species, a mold species, gram-positive bacteria, or gram-negative bacteria. Suitable contaminating microorganisms may include, without limitation, a *Rhodotorula* species, a *Lactobacillus* species, a *Saccharomyces* species, *Zygosaccharomyces* species, a *Candida* species, a *Leuconostoc* species, a *Lactococcus* species, and a *Pediococcus* species.

"Effective amount" is intended to mean an amount of a fermentate described herein sufficient to inhibit the growth of a contaminating microorganism on a food product by, for example, 10%, 20%, 50%, 75%, 80%, 90%, 95%, or 1-fold, 3-fold, 5-fold, 10-fold, 20-fold, or more compared to a negative control. In some embodiments, the effective amount of a fermentate may be between about 0.1% and about 5%. A "negative control" refers to a sample that serves as a reference for comparison to a test sample. For example, a test sample can be taken from a test condition including the presence of a fermentate and compared to negative control samples lacking the fermentate. One of skill in the art will recognize that controls can be designed for assessment of any number of parameters.

As noted above, a "food product" may include any food product susceptible to microbial contamination or degradation, and the suitable food products listed above apply equally here. The food product may have a pH between about 3 and about 8, and a water activity greater than 0.6.

Illustrative Embodiments

The following embodiments are illustrative and should not be interpreted to limit the scope of the claimed subject matter.

Embodiment 1. A fermentate from a fermenting microorganism.

Embodiment 2. The fermentate of embodiment 1, further comprising reuterin (β-hydroxypropionaldehyde).

Embodiment 3. The fermentate of embodiment 2, wherein the reuterin is at a concentration between about 5 mil and about 50 mM.

Embodiment 4. The fermentate of any one of the preceding embodiments, further comprising at least one metabolite selected from the group consisting of 1,3 propanediol (1,3 PPD) (aka trimethylene glycol (TMG)) and β-hydroxypropionic acid (β-HPA).

Embodiment 5. The fermentate of any one of the preceding embodiments, further comprising at least one metabolite selected from the group consisting of ethanol, lactate, and lactic acid.

Embodiment 6. The fermentate of any one of the preceding embodiments, further comprising a salt of lactate.

Embodiment 7. The fermentate of embodiment 6, wherein the salt of lactate is at a concentration about 0.01 mM and about 500 mM.

Embodiment 8. The fermentate of any one of embodiments 6-7, wherein the salt of lactate is calcium lactate.

Embodiment 9. The fermentate of any one of the preceding embodiments, wherein the fermenting microorganism is *Lactobacillus' reuteri*.

Embodiment 10. The fermentate of any one of the preceding embodiments, wherein the fermentate is a concentrated liquid.

Embodiment 11. The fermentate of any one of the preceding embodiments, wherein the fermentate is a dry powder.

Embodiment 12. The fermentate of any one of the preceding embodiments, wherein the fermentate has a pH between about 3 and about 8.

Embodiment 13. A method for producing a fermentate having antimicrobial activity comprising:
(a) making or obtaining a first liquid composition having a pH between 3 and 8, the first liquid composition comprising a fermentable carbohydrate, *Lactobacillus reuteri*, water, a growth media capable of supporting the growth of the *Lactobacillus reuteri*;
(b) incubating the first liquid composition under anaerobic conditions at a temperature for a first time period to produce a second liquid composition having a pH;
(c) adding glycerol and/or a base to the second liquid composition; and
(d) incubating the second liquid composition under anaerobic conditions at the temperature for a second time period to produce a first fermentate.

Embodiment 14. The method of embodiment 13, further comprising evaporating e first fermentate to produce a second fermentate.

Embodiment 15. The method of embodiment 14, further comprising spray-drying the second fermentate to produce a powdered fermentate.

Embodiment 16. The method of any one of embodiments 13-15, wherein the first liquid composition lacks glycerol.

Embodiment 17. The method of embodiment 16, wherein the first time period is between about 10 and about 12 hours.

Embodiment 18. The method of any one of embodiments 16-17, wherein the glycerol and/or the base is added to the second liquid composition when the pH of the second liquid composition drops below a pH of 5.

Embodiment 19. The method of any one of embodiments 13-18, wherein the base is calcium hydroxide.

Embodiment 20. The method of any one of embodiments 13-19, wherein the temperature is between about 28° C. and about 32° C.

Embodiment 21. The method of any one of embodiments 13-20, wherein the summation of the first time period and the second time period is between about 22 hours and about 26 hours.

Embodiment 22. The method of any one of embodiments 13-21, wherein the pH of the first liquid composition is about 5.

Embodiment 23. The method of any one of embodiments 13-22, wherein the fermentable carbohydrate is at a concentration between about 10 mM and about 500 mM in the first liquid composition.

Embodiment 24. The method of any one of embodiments 13-23, wherein the glycerol is at a final concentration between about 100 mM and about 400 mM in the second liquid composition. Embodiment 25. The method of any one of embodiments 13-24, wherein the fermentable carbohydrate is dextrose.

Embodiment 26. A food product comprising any one of the fermentates of embodiments 1-12.

Embodiment 27. The food product of embodiment 26, wherein the food product has a pH between about 3 and about 8.

Embodiment 28. The food product of any one of embodiments 26-27, wherein the food product has a water activity greater than 0.6.

Embodiment 29. The food product of any one of embodiments 26-28, wherein the food product is selected from the group consisting of culinary items, bakery items, cereals, pasta, meats, dairy items, rice, fish, nuts, beverages, confections, pet food, fruits, and vegetables.

Embodiment 30. A method for inhibiting the growth of a contaminating microorganism on a food product comprising:
making or obtaining any one of the fermentates of embodiments 1-12; and
applying an effective amount of the fermentate to at least one surface of the food product so as to inhibit the growth of the contaminating microorganism on the food product.

Embodiment 31. The method of embodiment 30, wherein the fermentate is applied in an amount between about 0.1% and about 5%.

Embodiment 32. The method of any one of embodiments 30-31, wherein the contaminating microorganism is selected from the group consisting of a yeast species, a mold species, a gram positive bacteria, and a gram negative bacteria.

Embodiment 33. The method of embodiment 32, wherein the contaminating microorganism is selected from the group consisting of a *Rhodotorula* species, a *Lactobacillus* species, a *Saccharomyces* species, *Zygosaccharomyces* species, a *Candida* species, a *Leuconostoc* species, a *Lactococcus* species, and a *Pedioccocus* species.

Embodiment 34. The method of any one of embodiments 30-33, wherein the food product is selected from the group consisting of culinary items, bakery items, cereals, pasta, meats, dairy items, rice, fish, nuts, beverages, confections, pet food, fruits, and vegetables.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise dearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1 mM to 50 mM, it is intended that values such as 2 mM to 40 mM, 10 mM to 30 mM, or 1 mM to 3 mM, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1: Production of One-Stage *Lactobacillus reuteri* Fermentates

Pure culture *L. reuteri* is grown anaerobically in DeMan, Rogosa, Sharpe (MRS) broth for approximately 6 hours and used as the starter culture for fermentation. A 2-liter benchtop fermentor is prepared with the following sterile components: 1-5% carbohydrate source (Sugar, Dextrose, etc.), 1-5% yeast extract, 0-5% glycerol, and less than 1% of trace minerals and salt solutions.

The fermentation vessel is set to agitate between 50-200 rpm, 25-37° C., and at a starting pH between 6.0 and 7.5 and allowed to lower naturally during growth to a pH between 4.0 and 6.0 and held within this range for the remainder of fermentation. The pH is maintained using a 5-25% base solution. The fermentation is run anaerobically using Nitrogen gas that is either sparged through the media or set to gas over the headspace of the vessel. The fermentation starts once the vessel is inoculated with 1% of the 6-hour growth culture of *L. reuteri*.

Typical fermentation is complete after 24 hours at which time a liquid sample is taken for activity. The liquid sample is centrifuged to pellet growth and the resulting liquid is filter-sterilized and collected for analysis. The remaining liquid can be spray dried with a lab scale spray dryer. A sample of the spray dried material is reconstituted at a concentration of 10-25% in sterile water then centrifuged and the resulting liquid is filter-sterilized and collected for analysis.

Example 2: Production of Two-Stage *Lactobacillus reuteri* Fermentates

A pure culture of *L. reuteri* was cultured in MRS (deMan, Rogosa, Sharpe) broth incubated anaerobically at 37° C. for 24 hours. Growth culture was concentrated via centrifugation and the pellet washed twice with sterile Sodium Phosphate buffer [137 mM NaCl, 2.7 mM KCl, 10 mM $Na_2HPO_4$, 1.7 mM $KH_2PO_4$, pH 7.40.]. The cells were resuspended in one-tenth initial volume with 250 mM sterile glycerol and incubated anaerobically at 37° C. for 2 hours. The culture was pelleted and the liquid was filter-sterilized through a 0.22 μm filter.

Example 3: One-Stage *Lactobacillus reuteri* Fermentates Contain Relatively Unpure Forms of Reuterin Compared to Two-Stage *Lactobacillus reuteri* Fermentates To compare the chemical compositions produced by a one-stage fermentation process to a two-stage fermentation process, we performed an HPLC analysis of fermentates produced by each process described in Examples 1 and 2. See FIG. 1. FIG. 1 shows that the two-stage process produces a relatively pure fermentate including reuterin (Black). On the contrary, the one-stage fermentation produces a relatively unpurified fermentate including reuterin and several additional unpurified by-products.

Example 4: Lowering the Fermentation Temperature Improves the Antimicrobial Activity of One-Stage *Lactobacillus reuteri* Fermentates Fermentations were run side-by-side with the exact same parameters except the temperature was set to 30° C., 32° C., and 35° C. Fermentations were run for 24 hours and samples were taken at 16 hours, 20 hours, and 24 hours. Samples were centrifuged and the resulting liquid was filter-sterilized.

Filtered products were tested for activity against indicator organism *Saccharomyces cervesiae* strain Y-1545 (obtained from the ARS-USDA NRRL culture collection) using a serial dilution assay. In brief, strain Y-1545 was grown in Potato Dextrose Broth (PDB) at 32° C. for 24 hours then diluted to a 0.5 McFarland in PDB. The assay is set up in a 96-well low profile clear assay plate with wells in row A filled with 180 µl PDB and wells in rows B-G filled with 100 µl PDB, A 20 µl volume of the filtered test sample is added to wells in row A and mixed gently with a pipette, resulting in a test concentration of 10%. Extra wells in row A should be saved for positive and negative controls which are inoculated with 20 µl of filtered fermentation media prior to inoculation. Serial dilutions are then made by transferring 100 µl from row A to row B and mixed gently, then 100 µl from row B transferred to row C and mixed gently, and so on until 100 µl is added to row G, mixed gently and then 100 µl removed from row G so all wells contain 100 µl total with the following test concentrations: 10%, 5%, 2.5%, 1.25%, 0.63%, 0.31%, 0.16%. All wells, except for the negative control wells, are inoculated with 2 µl of diluted Y-1545. The assay plate is covered with a clear plate seal and cover and incubated at 32 C for 16-20 hours. The optical density (OD) of the assay plate is measured by first gently mixing all wells with a pipette and then read on a plate reader at 600 nm wavelength.

As shown in Table 1, the 30° C. and 32° C. fermentations were able to be diluted down to 1.25% and prevent the growth of the indicator *S. cerevisiae*, strain 1545, however, the fermentation at 35° C. could only be diluted to 2.5% to prevent growth of the indicator strain. In both the 32° C. and 35° C. fermentations, activity was less effective after 16 hours.

Example 5: Glycerol Addition Following the Start of Fermentation Improves the Antimicrobial Activity of One-Stage *Lactobacillus reuteri* Fermentates The experiment in this example tested activity when glycerol was added as an ingredient at the start of fermentation (A) compared to glycerol being added with the base that was used to maintain pH (B). Fermentations were run side-by-side with the exact same parameters except those listed above. Both fermentations were run for 24 hours. In the fermentation where glycerol was added at the start, the fermentation actively took up base for 15 hours, whereas in the fermentation where glycerol was added with the base, the fermentation actively took up base for 11.5 hours. A liquid sample from each fermentation was taken at 24 hours, centrifuged and filter-sterilized. A liquid sample from each fermentation was spray dried then reconstituted at a concentration of 25%, centrifuged, and the resulting liquid filter-sterilized. The filtered liquid and spray dried products were tested for activity against indicator organism *Saccharomyces cervesiae* strain Y-1545 using a serial dilution assay (procedure same as described in Example 4).

As shown in Table 2, the liquid fermentate where glycerol was added at the start of fermentation (A) was active against the indicator strain, Y-1545, at a dilution of 5%, whereas, the fermentation where glycerol was added with the base (B) was active when diluted to 1.25%. The activity of the spray dried material was lost in the spray dried material where glycerol was added at the start of fermentation (A) but the activity was retained in the fermentation where glycerol was added with the base (B).

TABLE 1

Effect of Fermentation Temperature on Antimicrobial Activity of Fermentate
Optical density of yeast strain Y-1545 when grown in the presence of *L. reuteri*
fermentate grown at 30° C., 32° C. and 35° C. after 16, 20 and 24 hour growth.

| | 30 C. | | | 32 C. | | |
|---|---|---|---|---|---|---|
| 1545 | 16 h | 20 h | 24 h | 16 h | 20 h | 24 h |
| 10% | 0.044 | 0.044 | 0.055 | 0.042 | 0.042 | 0.044 |
| 5.0% | 0.043 | 0.042 | 0.042 | 0.042 | 0.042 | 0.042 |
| 2.5% | 0.328 | 0.041 | 0.041 | 0.042 | 0.169 | 0.342 |
| 1.25% | 0.422 | 0.13 | 0.106 | 0.109 | 0.374 | 0.403 |
| 0.63% | 0.486 | 0.4 | 0.375 | 0.456 | 0.468 | 0.494 |
| 0.31% | 0.447 | 0.403 | 0.418 | 0.44 | 0.442 | 0.412 |
| 0.16% | 0.448 | 0.416 | 0.394 | 0.387 | 0.396 | 0.441 |
| Empty | 0.048 | 0.047 | 0.047 | 0.046 | 0.045 | 0.047 |

| | 35 C. | | | | |
|---|---|---|---|---|---|
| 1545 | 16h | 20h | 24h | + | − |
| 10% | 0.043 | 0.043 | 0.043 | 0.658 | 0.042 |
| 5.0% | 0.043 | 0.054 | 0.124 | 0.661 | 0.041 |
| 2.5% | 0.117 | 0.434 | 0.388 | 0.641 | 0.041 |
| 1.25% | 0.398 | 0.5 | 0.519 | 0.553 | 0.041 |
| 0.63% | 0.455 | 0.495 | 0.515 | 0.485 | 0.041 |
| 0.31% | 0.405 | 0.416 | 0.421 | 0.414 | 0.041 |
| 0.16% | 0.393 | 0.421 | 0.378 | 0.438 | 0.041 |
| Empty | 0.046 | 0.047 | 0.049 | 0.046 | 0.047 |

TABLE 2

Timing of Glycerol Addition
Optical density of yeast strain Y-1545 when grown in the presence of
liquid and spray dried *L. reuteri* fermentate. (A) glycerol added at the start
of fermentation and (B) glycerol added with the base used to maintain pH.

Liquid Fermentate

| Y-1545 | A-glycerol at start | | B-glycerol with base | |
|---|---|---|---|---|
| 10% | 0.045 | 0.042 | 0.042 | 0.042 |
| 5.0% | 0.094 | 0.090 | 0.042 | 0.043 |
| 2.5% | 0.357 | 0.359 | 0.042 | 0.041 |
| 1.25% | 0.495 | 0.455 | 0.053 | 0.043 |
| 0.63% | 0.464 | 0.481 | 0.324 | 0.301 |
| 0.31% | 0.481 | 0.471 | 0.429 | 0.427 |
| 0.16% | 0.462 | 0.449 | 0.435 | 0.433 |
| Empty | 0.048 | 0.048 | 0.048 | 0.049 |

Spray Dried Fermentate

| | A-glycerol at start | | B-glycerol with base | | +control | | −control | |
|---|---|---|---|---|---|---|---|---|
| 2.5% | 0.493 | 0.525 | 0.042 | 0.045 | 0.483 | 0.494 | 0.041 | 0.042 |
| 1.25% | 0.554 | 0.567 | 0.042 | 0.042 | 0.429 | 0.469 | 0.041 | 0.043 |
| 0.63% | 0.552 | 0.534 | 0.253 | 0.218 | 0.427 | 0.448 | 0.041 | 0.042 |
| 0.31% | 0.541 | 0.538 | 0.449 | 0.441 | 0.405 | 0.408 | 0.040 | 0.041 |
| 0.16% | 0.499 | 0.479 | 0.471 | 0.459 | 0.399 | 0.421 | 0.040 | 0.040 |
| 0.08% | 0.464 | 0.471 | 0.453 | 0.453 | 0.442 | 0.441 | 0.040 | 0.041 |
| 0.04% | 0.447 | 0.441 | 0.457 | 0.456 | 0.424 | 0.427 | 0.043 | 0.042 |
| Empty | 0.048 | 0.046 | 0.046 | 0.048 | 0.049 | 0.046 | 0.047 | 0.049 |

Example 6: Different Bases can be Used for Fermentation of *Lactobacillus reuteri*

Fermentations can run effectively using different bases for pH control. In the following example the fermentation was performed side-by-side using the same exact parameters except different bases were used for pH control, CaOH, NH$_3$OH, and KOH. Fermentations were run for 24 hours and liquid samples were taken at 16 hours, 20 hours, and 24 hours. Samples were centrifuged and the resulting liquid was filter-sterilized and collected. Filtered liquid samples were tested for activity against indicator organism *Saccharomyces cervesiae* strain Y-1545 using a serial dilution assay (procedure same as described in Example 4).

As shown in Table 3, the liquid fermentate that used CaOH or KOH had activity down to 2.5% at 20 hours, whereas, the fermentate that used NH$_3$OH took 24 hours to reach the same activity level in the ability to prevent the growth of the indicator *S. cerevisiae*, strain Y-1545.

TABLE 3

Optical density of yeast strain Y1545 when grown in the presence of *L. reuteri*
fermentate grown in the presence of different bases after 16, 20, and 24 hour growth.

| | CaOH | | | NH$_3$OH | | |
|---|---|---|---|---|---|---|
| Y-1545 | 16 h | 20 h | 24 h | 16 h | 20 h | 24 h |
| 10% | 0.044 | 0.043 | 0.043 | 0.289 | 0.045 | 0.045 |
| 5.0% | 0.274 | 0.042 | 0.042 | 0.65 | 0.06 | 0.043 |
| 2.5% | 0.586 | 0.194 | 0.209 | 0.708 | 0.57 | 0.279 |
| 1.3% | 0.619 | 0.526 | 0.543 | 0.665 | 0.611 | 0.517 |
| 0.63% | 0.553 | 0.542 | 0.542 | 0.608 | 0.594 | 0.563 |
| 0.31% | 0.518 | 0.519 | 0.507 | 0.502 | 0.566 | 0.539 |
| 0.16% | 0.502 | 0.492 | 0.49 | 0.529 | 0.52 | 0.506 |
| Empty | 0.046 | 0.046 | 0.047 | 0.048 | 0.047 | 0.047 |

| | KOH | | | | |
|---|---|---|---|---|---|
| Y-1545 | 16 h | 20 h | 24 h | + | − |
| 10% | 0.044 | 0.055 | 0.045 | 0.781 | 0.047 |
| 5.0% | 0.334 | 0.043 | 0.042 | 0.763 | 0.043 |
| 2.5% | 0.637 | 0.06 | 0.043 | 0.723 | 0.041 |
| 1.3% | 0.625 | 0.501 | 0.443 | 0.613 | 0.041 |
| 0.63% | 0.583 | 0.531 | 0.56 | 0.605 | 0.041 |
| 0.31% | 0.552 | 0.533 | 0.548 | 0.552 | 0.04 |
| 0.16% | 0.529 | 0.526 | 0.516 | 0.493 | 0.041 |
| Empty | 0.046 | 0.047 | 0.046 | 0.046 | 0.047 |

Sodium hydroxide is not commonly used for commercial production of *Lactobacillus* fermentates due to the production of sodium lactate during fermentation which is has high viscosity and syrup-like attributes. In the following experiment, the fermentation was performed side-by-side using the same exact parameters except different bases were used for pH control; CaOH, NaOH, KOH, and NH$_3$OH. A liquid sample from each fermentation was taken at 24 hours, centrifuged and filter-sterilized. A liquid sample from each fermentation was spray dried then reconstituted at a concentration of 25%, centrifuged, and the resulting liquid filter-sterilized. The filtered liquid and spray dried products were tested for activity against indicator organism *Saccharomyces cervesiae* strain Y-1545 using a serial dilution assay (procedure same as described in Example 4).

As shown in Table 4, the liquid fermentates had similar activity regardless of the base used for fermentation, with slightly better activity shown in the fermentate with NH$_3$OH. After spray drying, the fermentate with NaOH was able to be diluted further than fermentates using CaOH, KOH, and NH$_3$OH in the ability to prevent the growth of the indicator *S. cerevisiae*, strain Y-1545.

Example 7: One-Stage *Lactobacillus reuteri* Fermentates Inhibit or Kill Various Microorganisms A single-stage *L. reuteri* fermentation was performed and a sample at 24 hours was centrifuged and the resulting liquid was filter-sterilized. A 10% solution of a commercial *Lactococcus lactis* spray dried fermentate was prepared and filter-sterilized. These two test solutions were tested against a variety of yeast and Gram-positive bacteria in a 96-well assay. Control wells contained 100 ul broth and test wells contained 90 ul broth and 10 ul of test material resulting in final test concentrations of 10% for liquid *L. reuteri* fermentation and for spray dried *L. lactis* fermentation. All test wells and positive control wells were inoculated with 2 µl of indicator organisms, covered with a clear plate seal and cover and incubated at 32° C. for 16-20 hours. The assay for. Gram-positive indicators used MRS broth and assay plates were incubated anaerobically. The assay for yeast indicators used PDB and assay plates were incubated aerobically. After incubation the optical density was measured at 600 nm wavelength and the percent inhibtion was calculated. Table 5 shows data for the commercial *L. lactis* fermentate (A) and *L. reuteri* fermentate (B). In general, the inhibition of Gram-positive was either inhibited by the *L. lactis* fermentate or the *L. reuteri* fermentate with little to no inhibition by both against the same indicator strain. Certain yeasts were only inhibited by the *L. reuteri* fermentate.

TABLE 4

Optical density of yeast strain Y-1545 when grown in the presence of liquid (A) and spray dried (B) *L. reuteri* fermentate grown in the presence of different bases after 24-hours.

A

| Liquid | CaOH | | NaOH | | KOH | | NH$_3$OH | | + | | − | |
|---|---|---|---|---|---|---|---|---|---|---|---|---|
| 10% | 0.043 | 0.042 | 0.043 | 0.048 | 0.041 | 0.041 | 0.041 | 0.042 | 0.375 | 0.461 | 0.04 | 0.041 |
| 5.0% | 0.043 | 0.042 | 0.041 | 0.041 | 0.041 | 0.041 | 0.041 | 0.041 | 0.387 | 0.394 | 0.041 | 0.041 |
| 2.5% | 0.042 | 0.042 | 0.041 | 0.042 | 0.042 | 0.041 | 0.041 | 0.043 | 0.355 | 0.368 | 0.041 | 0.04 |
| 1.25% | 0.083 | 0.043 | 0.045 | 0.044 | 0.042 | 0.042 | 0.043 | 0.041 | 0.429 | 0.334 | 0.04 | 0.04 |
| 0.63% | 0.203 | 0.217 | 0.195 | 0.181 | 0.196 | 0.12 | 0.09 | 0.096 | 0.358 | 0.351 | 0.04 | 0.04 |
| 0.31% | 0.353 | 0.355 | 0.321 | 0.338 | 0.297 | 0.292 | 0.278 | 0.288 | 0.382 | 0.381 | 0.04 | 0.041 |
| 0.16% | 0.387 | 0.391 | 0.37 | 0.379 | 0.306 | 0.359 | 0.375 | 0.384 | 0.363 | 0.376 | 0.04 | 0.042 |
| Empty | 0.048 | 0.048 | 0.049 | 0.05 | 0.048 | 0.047 | 0.047 | 0.047 | 0.049 | 0.047 | 0.047 | 0.048 |

(B)

| Spray Dry | CaOH | | NaOH | | KOH | | NH$_3$OH | | + | | − | |
|---|---|---|---|---|---|---|---|---|---|---|---|---|
| 2.5% | 0.101 | 0.043 | 0.043 | 0.045 | 0.057 | 0.063 | 0.045 | 0.048 | 0.478 | 0.431 | 0.041 | 0.044 |
| 1.25% | 0.152 | 0.096 | 0.043 | 0.044 | 0.126 | 0.116 | 0.077 | 0.075 | 0.394 | 0.378 | 0.041 | 0.042 |
| 0.63% | 0.304 | 0.302 | 0.051 | 0.045 | 0.285 | 0.297 | 0.247 | 0.241 | 0.367 | 0.36 | 0.041 | 0.041 |
| 0.31% | 0.482 | 0.377 | 0.207 | 0.196 | 0.362 | 0.376 | 0.36 | 0.351 | 0.351 | 0.303 | 0.04 | 0.04 |
| 0.16% | 0.401 | 0.413 | 0.354 | 0.346 | 0.365 | 0.404 | 0.378 | 0.356 | 0.338 | 0.307 | 0.041 | 0.041 |
| 0.08% | 0.45 | 0.415 | 0.396 | 0.416 | 0.382 | 0.397 | 0.389 | 0.375 | 0.374 | 0.365 | 0.041 | 0.041 |
| 0.04% | 0.405 | 0.411 | 0.407 | 0.421 | 0.397 | 0.396 | 0.388 | 0.393 | 0.392 | 0.353 | 0.041 | 0.042 |
| Empty | 0.048 | 0.048 | 0.048 | 0.049 | 0.048 | 0.047 | 0.047 | 0.048 | 0.049 | 0.048 | 0.047 | 0.049 |

TABLE 5

(A) Percent inhibition of various yeast and Gram (+) bacteria with a commercial bacterial fermentate produced from *Lactococcus lactis*. The strains showing less than 60% inhibition in column (A) were not sufficiently control by the *L lactis* fermentate product. These same strains, however, were filly-inhibited in column (B), which contains the single stage fermentation *L. reuteri* fermentate. Also, note that none of the yeast (yellow highlight) are controlled by the *L. lactis* fermentate. But, they were all controlled with the *L. reuteri* fermentate.

|  | A | B |
|---|---|---|
| *Rhodotorula mucilaginosa* | 56.1% | 100.0% |
| *Lactobacillus casei* | 26.5% | 99.7% |
| *Lactobacillus paracasei* | 22.7% | 99.6% |
| *Lactobacillus pentosus* | 17.7% | 99.4% |
| *Lactobacillus paracasei* | 30.2% | 99.3% |
| *Lactobacillus paracasei* | 19.6% | 99.2% |
| *Saccharomyces cerevisiae* | 0.0% | 99.2% |
| *Lactobacillus paracasei* | 23.4% | 99.1% |
| *Lactobacillus paracasei* | 0.0% | 98.9% |
| *Lactobacillus casei* | 19.8% | 98.9% |
| *Zygosaccharomyces bisporus* | 6.8% | 98.5% |
| *Zygosaccharomyces bailii* | 8.1% | 98.4% |
| *Lactobacillus paracasei* | 25.7% | 98.1% |
| *Lactobacillus casei* | 11.5% | 98% |
| *Candida parapsilosis* | 29% | 97.9% |
| *Lactobacillus paracasei* | 0.0% | 97.9% |
| *Lactobacillus paracasei* | 28% | 97.2% |
| *Lactobacillus graminis* | 98.8% | 79.5% |
| *Lactobacillus coryniformis* | 99.4% | 69.6% |
| *Leuconostoc pseudomesenteroides* | 99.4% | 54.7% |
| *Lactobacillus sakei* | 98.9% | 53.3% |
| *Lactobacillus coryniformis* | 99.6% | 38.9% |
| *Lactobacillus sakei* | 99.7% | 37.5% |
| *Lactococcus lactis* | 99.7% | 32.7% |
| *Pediococcus parvulus* | 88.3% | 28.0% |

Example 8: One-Stage *Lactobacillus reuteri* Fermentates Inhibit or Kill the Indicator Microorganism—*Saccharomyces cerevisiae*—at Various pHs A single-stage *L. reuteri* fermentation was performed and completed at 24 hours at which time a sample of liquid fermentate was collected, centrifuged and the resulting liquid was filter-sterilized. A liquid fermentate sample was also spray dried and rehydrated in sterile water at 25% then centrifuged and the resulting liquid was filter-sterilized. The filtered spray dried solution and the initial filtered liquid fermentation were tested in a serial dilution assay against indicator *S. cerevisiae*, strain Y-1545, in PDB adjusted to pH 4.0, 5.0, 6.0, and 7.0. The assay was set up as described in Example 4. The data in Table 6 shows the inhibition of the indicator organism when grown in broth media at pH 4, 5, 6, and 7 when testing the liquid (A) or spray dried (B) fermentate.

TABLE 6

Percent inhibition of *Saccharomyces cerevisiae*, strain Y-1545, after growth in media adjusted to various pH levels and in the presence of serially diluted liquid (A) and spray dried (B) *L. reuteri* fermentate after 24 hours of growth.

| (A) | | | | |
|---|---|---|---|---|
| Liquid | pH 4.0 | pH 5.0 | pH 6.0 | pH 7.0 |
| 10% | 99.3% | 100.2% | 99.6% | 100.2% |
| 5.0% | 100.7% | 100.2% | 99.6% | 100.2% |
| 2.5% | 101.4% | 100.2% | 100.0% | 99.8% |
| 1.25% | 72.9% | 94.3% | 84.3% | 97.1% |
| 0.63% | 19.3% | 28.8% | 33.0% | 20.8% |
| 0.31% | 0.0% | 12.4% | 4.4% | 7.0% |
| 0.16% | 0.0% | 0.0% | 16.3% | 0.0% |

| (B) | | | | |
|---|---|---|---|---|
| Spray Dried | pH 4.0 | pH 5.0 | pH 6.0 | pH 7.0 |
| 2.5% | 99.6% | 99.2% | 99.4% | 99.8% |
| 1.25% | 79.0% | 100.0% | 99.6% | 100.0% |
| 0.63% | 0.0% | 60.0% | 94.8% | 99.3% |
| 0.31% | 0.0% | 17.2% | 27.9% | 44.9% |
| 0.16% | 0.0% | 30.5% | 10.5% | 16.1% |
| 0.08% | 0.0% | 17.2% | 3.7% | 3.5% |
| 0.04% | 0.0% | 0.0% | 0.0% | 6.3% |

Example 9: One-Stage *Lactobacillus reuteri* Fermentates Inhibit or Kill Multiple Yeast Strains at Various pHs Two separate single-stage *L. reuteri* fermentations were performed and completed at 24 hours at which time the fermentate material was spray dried. The *L. reuteri* spray dried materials (LR1 and LR2), as well as two commercially available dried fermentation products (C1 and C2), were rehydrated at 10% then centrifuged and the resulting liquid was filter-sterilized. The filtered solutions were all tested at a concentration of 1% against six yeast strains in PDB adjusted to pH 5, 6, 7, and 8. The yeasts used in the assay were obtained from the USDA-ARS NRRL culture collection and are listed in Table 7. The assay was set up in a 96-well low profile clear assay plate in which test wells contained 90 ul PDB at various pHs, 10 ul of 10% filter-sterilized test solution, and 2 ul of overnight yeast growth diluted to a 1.0 McFarland standard. Positive control wells contained 100 ul PDB at various pHs and 2 ul of diluted yeast growth, and negative control wells contained 100 ul PDB at various pHs. Assay plates were sealed with an adhesive film and incubated at 30° C. overnight. As shown in Table 8, the yeast growth was prevented in the *L. reuteri* treated wells (LR1 and LR2) regardless of the pH of the media. The commercial fermentate products (C1 and C2) were able to control some yeast growth in media at pH 5.0 but unable to control most yeast in media at pH 6.0 and higher. There were a few yeast strains that were unable to grow at pH higher than 6.0.

TABLE 7

Yeast strains obtained from the USDA-ARS NRRL culture collection.

| NRRL | Strain Name | Source | Isolation Information |
|---|---|---|---|
| Y-1545 | *Saccharomyces cerevisiae* | Kreger-van Rij, CBS, Delft, The Netherlands | DFD—Stracchino Cheese—Italy |
| YB-619 | *Candida parapsilosis* | L. Wickerham, NRRL | FRT—Honeydew Melon |
| Y-866 | *Torulaspora delbrueckii* | Wallerstein Labs | |
| YB-632 | *Rhodotorula mucilaginosa* | L. Wickerham, NRRL | MFD—Lunch Meat |
| Y-7239 | *Zygosaccharomyces bailii* | Cletus Kurtzman, NRRL | SD—Salad Dressing |

TABLE 7-continued

Yeast strains obtained from the USDA-ARS NRRL culture collection.

| NRRL | Strain Name | Source | Isolation Information |
|---|---|---|---|
| Y-7253 | Zygosaccharomyces bisporus | C. Kurtzman, NRRL | SD—Spoiled Salad Dressing |

TABLE 8

Optical density at 600 nm of yeast strains grown overnight in the presence of commercial spray dried fermentates (C1 and C2) and *L. reuteri* spray dried fermentates (LR1 and LR2) at test concentrations of 1% in PDB adjusted to pH 5, 6, 7, and 8.

|  |  | C1 | | C2 | | LR1 | | LR2 | | + | − |
|---|---|---|---|---|---|---|---|---|---|---|---|
| Y-1545 | pH 5 | 0.4 | 0.425 | 0.447 | 0.442 | 0.441 | 0.415 | 0.147 | 0.121 | 0.459 | 0.042 |
|  | pH 6 | 0.419 | 0.429 | 0.47 | 0.444 | 0.335 | 0.325 | 0.083 | 0.066 | 0.469 | 0.041 |
|  | pH 7 | 0.394 | 0.404 | 0.459 | 0.432 | 0.253 | 0.19 | 0.063 | 0.048 | 0.394 | 0.04 |
|  | pH 8 | 0.402 | 0.393 | 0.456 | 0.421 | 0.171 | 0.12 | 0.045 | 0.042 | 0.275 | 0.041 |
| YB-619 | pH 5 | 0.179 | 0.177 | 0.198 | 0.178 | 0.054 | 0.051 | 0.043 | 0.042 | 0.281 | 0.041 |
|  | pH 6 | 0.189 | 0.206 | 0.2 | 0.228 | 0.047 | 0.045 | 0.043 | 0.042 | 0.278 | 0.04 |
|  | pH 7 | 0.224 | 0.224 | 0.237 | 0.233 | 0.043 | 0.043 | 0.042 | 0.041 | 0.275 | 0.042 |
|  | pH 8 | 0.208 | 0.204 | 0.243 | 0.239 | 0.043 | 0.042 | 0.043 | 0.042 | 0.263 | 0.041 |
| Y-866 | pH 5 | 0.548 | 0.566 | 0.644 | 0.587 | 0.476 | 0.504 | 0.294 | 0.158 | 0.716 | 0.041 |
|  | pH 6 | 0.56 | 0.576 | 0.604 | 0.576 | 0.42 | 0.405 | 0.114 | 0.09 | 0.605 | 0.041 |
|  | pH 7 | 0.524 | 0.509 | 0.655 | 0.653 | 0.318 | 0.327 | 0.101 | 0.067 | 0.632 | 0.04 |
|  | pH 8 | 0.637 | 0.578 | 0.638 | 0.64 | 0.176 | 0.239 | 0.051 | 0.046 | 0.611 | 0.04 |
| YB-632 | pH 5 | 0.094 | 0.099 | 0.093 | 0.094 | 0.068 | 0.066 | 0.043 | 0.043 | 0.123 | 0.04 |
|  | pH 6 | 0.098 | 0.1 | 0.104 | 0.1 | 0.064 | 0.06 | 0.043 | 0.042 | 0.123 | 0.041 |
|  | pH 7 | 0.112 | 0.113 | 0.111 | 0.111 | 0.056 | 0.051 | 0.042 | 0.042 | 0.116 | 0.042 |
|  | pH 8 | 0.107 | 0.108 | 0.11 | 0.108 | 0.048 | 0.047 | 0.045 | 0.042 | 0.115 | 0.041 |
| Y-7239 | pH 5 | 0.121 | 0.131 | 0.191 | 0.156 | 0.1 | 0.098 | 0.058 | 0.053 | 0.172 | 0.042 |
|  | pH 6 | 0.13 | 0.127 | 0.158 | 0.157 | 0.077 | 0.073 | 0.049 | 0.047 | 0.111 | 0.041 |
|  | pH 7 | 0.083 | 0.093 | 0.142 | 0.134 | 0.06 | 0.058 | 0.048 | 0.045 | 0.045 | 0.04 |
|  | pH 8 | 0.046 | 0.048 | 0.11 | 0.108 | 0.049 | 0.051 | 0.043 | 0.043 | 0.043 | 0.04 |
| Y-7253 | pH 5 | 0.192 | 0.198 | 0.169 | 0.182 | 0.068 | 0.072 | 0.043 | 0.043 | 0.206 | 0.04 |
|  | pH 6 | 0.181 | 0.176 | 0.168 | 0.162 | 0.054 | 0.052 | 0.043 | 0.042 | 0.197 | 0.04 |
|  | pH 7 | 0.07 | 0.072 | 0.1 | 0.099 | 0.045 | 0.045 | 0.042 | 0.041 | 0.063 | 0.042 |
|  | pH 8 | 0.043 | 0.043 | 0.067 | 0.068 | 0.043 | 0.042 | 0.044 | 0.042 | 0.044 | 0.042 |

Example 10—Fermentation of *Lactabacillus reuteri* can Delay Yeast Growth in a pH Neutral Chicken Stock During Challenge A container of natural chicken stock with no added preservatives was purchased from a retail grocery store. Two 500 ml glass bottles were filled with 110 ml chicken stock and 110 ml deionized water to dilute the chicken stock by 50% and steam sterilized at 121° C. at 15 psi pressure for 15 minutes. The contents of the bottles were allowed to cool to room temperature and then one bottle received 2.2 grams (1%) of *Lactobacillus reuteri* spray dried fermentate. Each bottle was then split into two sterile Erlenmeyer flasks, each receiving 100 ml chicken stock.

All four flasks were inoculated with a dual yeast challenge of *Candida parapsilosis* strain, Y-619, and *Torulaspora delbruckii* strain, Y-866, which were both obtained from the ARS NRRL Culture Collection. Yeast strains were grown in Potato Dextrose broth at 32° C. overnight, then diluted in sterile water to approximately $2.0 \times 10^4$ CFU/ml. The two strains were then combined and 1 ml of the combination culture was added to each flask to provide a challenge dose of approximately $2.0 \times 10^2$ CFU/ml.

A 2 ml sample was removed from each flask after challenge inoculation to analyze the pH and the initial yeast count in duplicate on Potato Dextrose Agar acidified with 10% Tartaric Acid (PDA+TA). Once solidified, the PDA+TA plates were incubated aerobically at 28° C. for 72 hours and then counted for colony forming units per nil (CFU/ml).

Flasks were incubated at room temperature (~25° C.), in a shaking incubator set at 100 rpm for the duration of the study. After 24, 48, and 72 hours a 2 ml sample was removed from each flask to analyze the change in pH and yeast count in duplicate on PDA+TA.

Results

Figure 2:
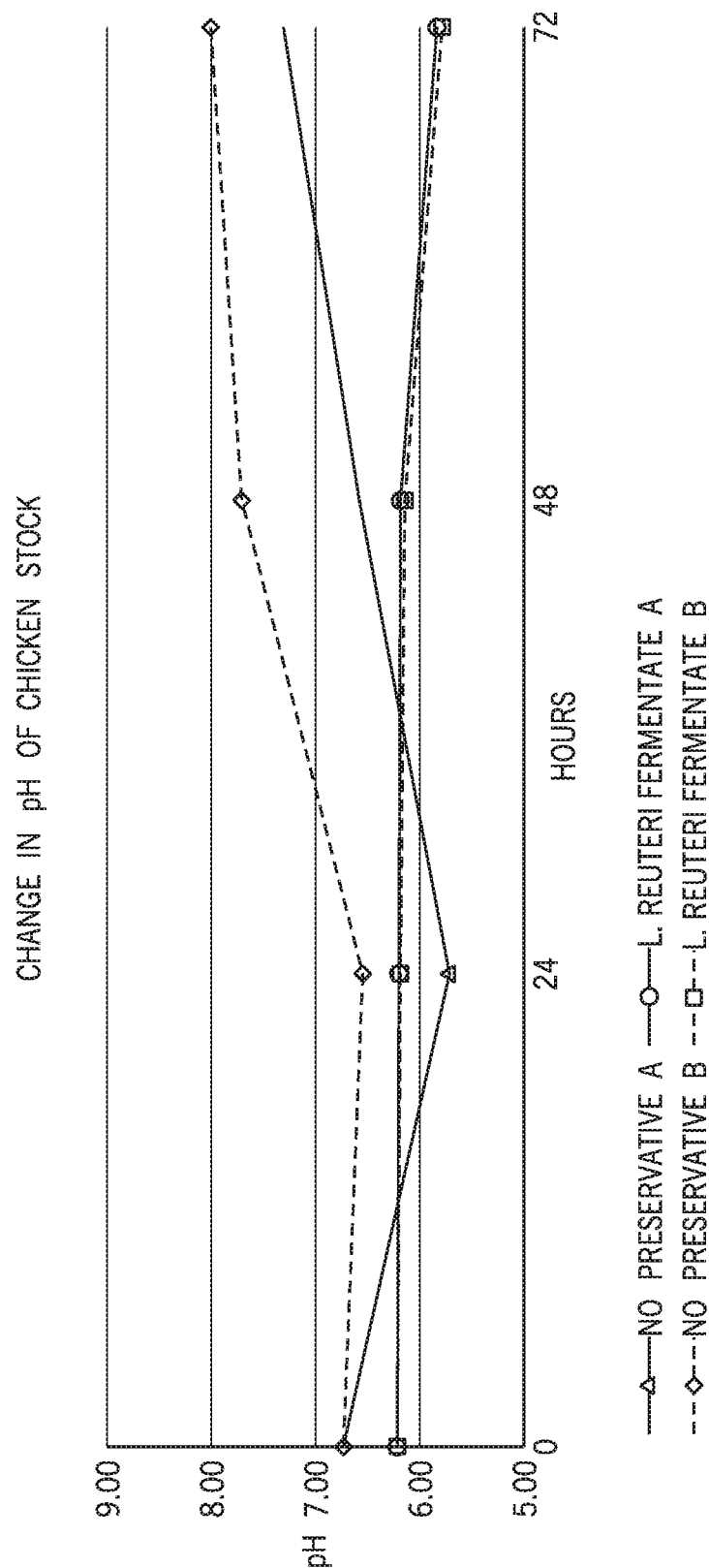
FIG. 2 shows the change in pH of chicken stock with and without the addition of *L. reuteri* fermentate over time.

The initial pH of the chicken broth with No Preservative was 6.73 and with the *L. reuteri* fermentate was 6.21 (Table 9). The pH in the duplicate flasks of the No Preservative treatment varied widely at each testing point with a difference of 0.68-1.12 pH units over time, however, the flasks did have a similar trend in pH (FIG. 2) with an initial drop at 24 hours and then a constant increase at 48 and 72 hours finishing at an average of 7.65 which was almost 1 pH unit above the initial pH. The pH in the duplicate flasks with the *L. reuteri* fermentate was within 0.1-0.3 pH units and had slight decreases in pH each day with a final pH of 5.80 by 72 hours which was 0.41 pH units below the initial pH.

TABLE 9 pH of chicken stock with and without addition of *L. reuteri* fermentate over time.

|  | No Preservative | | | | *L. reuteri* Fermentate | | | |
|---|---|---|---|---|---|---|---|---|
| Hours | Flask A | Flask B | AVG | STDEV | Flask A | Flask B | AVG | STDEV |
| 0 | 6.72 | 6.73 | 6.73 | 0.0 | 6.21 | 6.21 | 6.21 | 0.0 |
| 24 | 5.71 | 6.54 | 6.13 | 0.4 | 6.18 | 6.17 | 6.18 | 0.0 |
| 48 | 6.57 | 7.69 | 7.13 | 0.6 | 6.16 | 6.15 | 6.16 | 0.0 |
| 72 | 7.31 | 7.99 | 7.65 | 0.3 | 5.81 | 5.78 | 5.80 | 0.0 |

Figure 3:
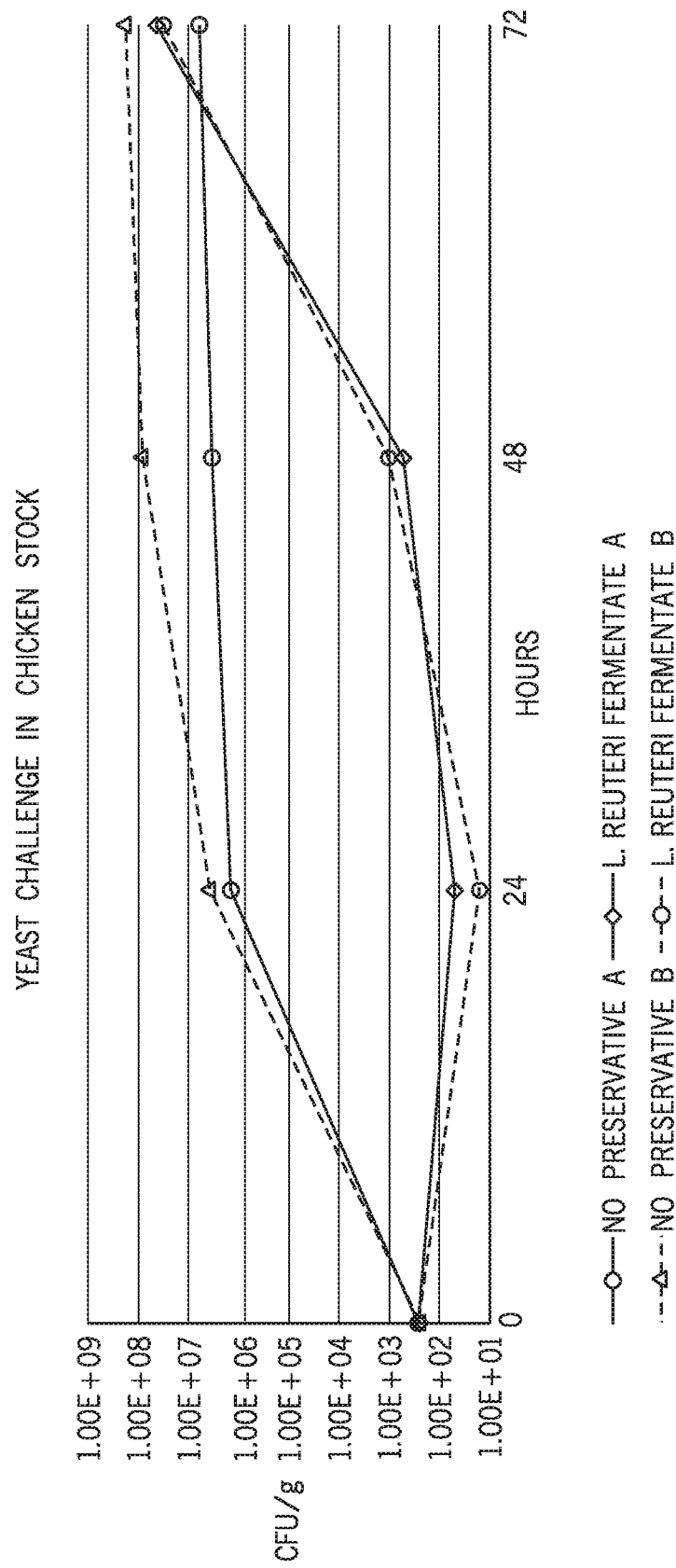
FIG. 3 shows the average enumeration of yeast in chicken stock with and without the addition of *L. reuteri* fermentate over time.

For yeast challenge studies, the chicken stock was sterilized prior to yeast challenge, therefore, only yeast was enumerated from each flask for the duration of the study (Table 10, FIG. 3). On the day of challenge, the flasks with No Preservative had an average of $2.5 \times 10^2$ CFU/ml and the *L. reuteri* treated flasks had an average of $2.4 \times 10^2$ CFU/ml, both of which were within the anticipated challenge dose. The yeast levels in the flasks with No Preservative had an immediate four-log increase at 24 hours with an average of $2.8 \times 10^6$ CFU/g. The yeast levels in the No Preservative began to level off in flask A by 48 hours, but increased in flask B through 72 hours and were approximately 1.5 logs higher than flask A during this time span. The *L. reuteri* treated flasks showed a delay in the outgrowth of yeast with an initial decrease at 24 hours and then increased to just above the initial challenge levels at 48 hours and then continued to increase to an average of $4.0 \times 10^7$ CFU/g at 72 hours.

TABLE 10

Enumeration of yeast in chicken stock over time with duplicate counts listed as colony forming units per ml (CFU/ml), averages, and standard deviation.

| | No Preservative | | | | | |
|---|---|---|---|---|---|---|
| Hours | Flask A (CFU/ml) | | Flask B (CFU/ml) | | AVG | STDEV |
| 0 | 2.20E+02 | 2.90E+02 | 2.10E+02 | 2.90E+02 | 2.53E+02 | 37.7 |
| 24 | 1.50E+06 | 1.55E+06 | 3.45E+06 | 4.81E+06 | 2.83E+06 | 1388531.1 |
| 48 | 3.30E+06 | 3.90E+06 | 9.32E+07 | 9.86E+07 | 4.98E+07 | 46189961.0 |
| 72 | 5.20E+06 | 7.40E+06 | 1.80E+08 | 2.20E+08 | 1.03E+08 | 97880169.1 |

| | L. reuteri fermentate | | | | | |
|---|---|---|---|---|---|---|
| Hours | Flask A (CFU/ml) | | Flask B (CFU/ml) | | AVG | STDEV |
| 0 | 2.00E+02 | 2.50E+02 | 2.50E+02 | 2.70E+02 | 2.43E+02 | 25.9 |
| 24 | 5.00E+01 | 5.00E+01 | 1.00E+01 | 2.00E+01 | 3.25E+01 | 441.9 |
| 48 | 2.00E+02 | 8.40E+02 | 7.40E+02 | 1.22E+03 | 7.50E+02 | 364.6 |
| 72 | 4.31E+07 | 4.63E+07 | 3.22E+07 | 3.92E+07 | 4.02E+07 | 5258802.1 |

Example 11—Fermentation of *Lactobacillus reuteri* can Reduce Yeast Challenge in a pH Neutral Dark Chocolate Sauce A dark chocolate sauce was manufactured with and without the addition of Potassium sorbate, a standard preservative used in this food. One sterile quart-size calming jar was filled with 980 grams of dark chocolate sauce with Potassium sorbate. The dark chocolate sauce without Potassium sorbate was divided into three sterile quart-sized canning jars each filled with 980 grams total and treated with either 1% Propionic acid-based fermentate, 1% *Lactobacillus reuteri* fermentate, or 1% *L. reuteri* fermentate heated to 60° C. The treatments were prepared by dissolving the spray dried fermentate in 15 ml sterile water and then mixed into the sauce using sterile hand whisks. One of the *L. reuteri* fermentate treatments was incubated for 30 minutes in a water bath set at 60° C. prior to addition to the chocolate sauce to determine how heat would affect the treatment since traditional manufacturing of the chocolate sauce includes a heating step. The dark chocolate sauce with Potassium sorbate received 15 ml sterile water to ensure all treatments had the same consistency.

All jars were then inoculated with a dual yeast challenge of *Zygosaccharomyces rouxii* strain, Y-229, and *Torulaspora delbruckii* strain, Y-866, which were both obtained from the ARS NRRL Culture Collection. The yeast strains were grown in Potato Dextrose broth at 32° C. overnight, then diluted in sterile water to approximately $2.0 \times 10^5$ CFU/ml. The two strains were then combined and 5 ml of the combination culture was added to each jar to provide a challenge dose of approximately $1.0 \times 10^3$ CFU/ml.

A 10-gram sample was removed from each jar immediately after challenge inoculation to analyze the pH and the initial yeast count in duplicate on Potato Dextrose Agar acidified with 10% Tartaric Acid (PDA4-TA) as well as the total aerobic plate count (APC) in duplicate on Tryptic Soy Agar (TSA). Once solidified, the PDA+TA plates were incubated at 28° C. for 72 hours and the TSA plates were incubated at 32° C. for 48 hours, then counted to determine CFU/g. The jars were kept at room temperature (~20-22° C.) in a dark cabinet for the first 21 days, then moved to an incubator set at 28° C. for the duration of the study. On days 4, 7, 11, 14, 18, 21, 28, 35, 49, 56, 63, 94, 109, and 124, a 10-gram sample was removed from each jar to analyze the change in pH, as well as the yeast and APC levels in duplicate as described above.

Results:

The starting pH of the chocolate sauce ranged from 6.53 to 6.63 and after 124 days the pH ranged from 6.52 to 6.59. Throughout the study the change in pH within a treatment varied less than 0.1 pH unit up or down (Table 11).

TABLE 11 pH of dark chocolate sauce with different preservative treatments over time.

| Days | Potassium sorbate | Propionic Acid Fermentate | L. reuteri Fermentate | L. reuteri Fermentate @ 60 C. |
|---|---|---|---|---|
| 0 | 6.58 | 6.63 | 6.53 | 6.53 |
| 4 | 6.56 | 6.63 | 6.54 | 6.54 |
| 7 | 6.60 | 6.65 | 6.55 | 6.55 |
| 11 | 6.58 | 6.64 | 6.55 | 6.54 |
| 14 | 6.59 | 6.64 | 6.56 | 6.55 |
| 18 | 6.58 | 6.62 | 6.54 | 6.54 |
| 21 | 6.57 | 6.62 | 6.56 | 6.53 |
| 28 | 6.58 | 6.63 | 6.56 | 6.55 |
| 35 | 6.56 | 6.59 | 6.53 | 6.51 |
| 49 | 6.57 | 6.63 | 6.55 | 6.55 |
| 56 | 6.60 | 6.64 | 6.56 | 6.55 |
| 63 | 6.57 | 6.62 | 6.55 | 6.55 |
| 94 | 6.59 | 6.70 | 6.55 | 6.54 |
| 109 | 6.53 | 6.58 | 6.52 | 6.52 |
| 124 | 6.54 | 6.59 | 6.52 | 6.56 |

Figure 4:
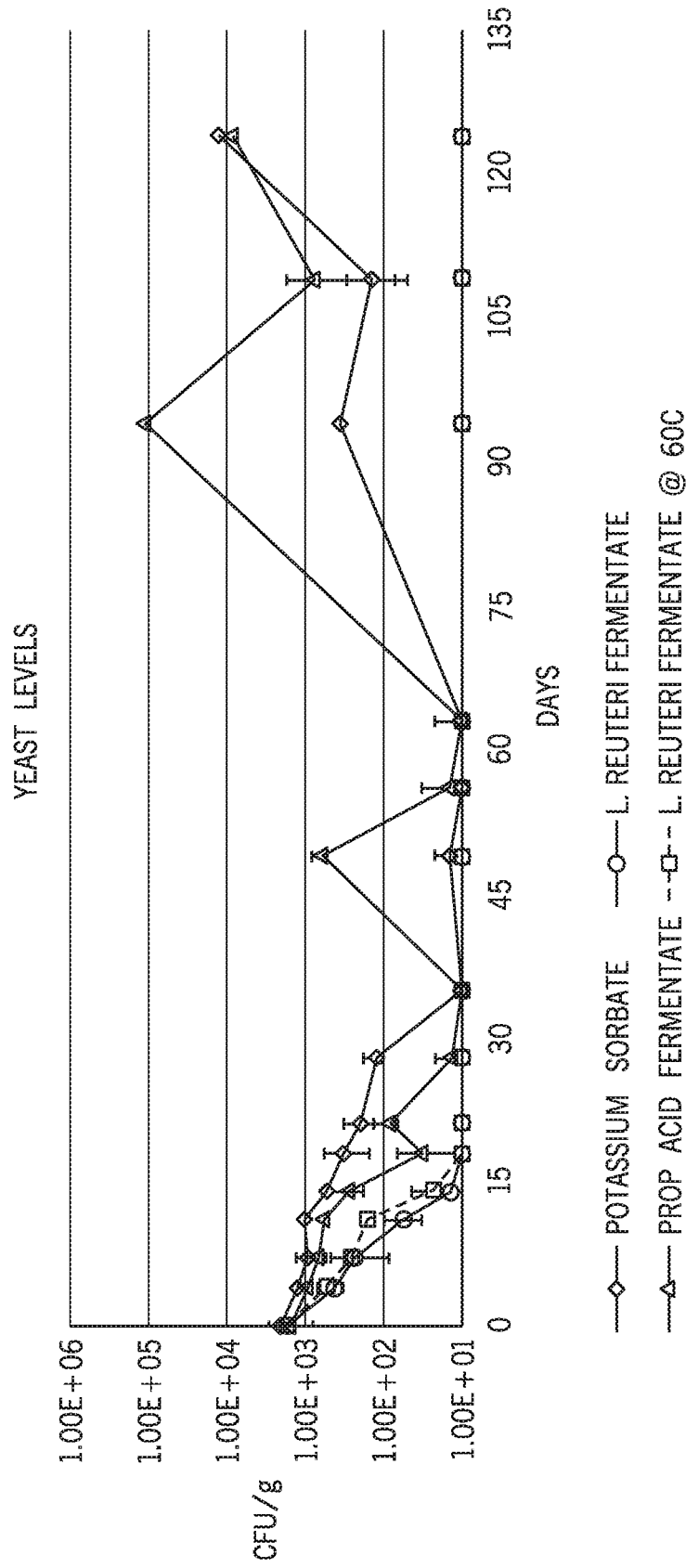
FIG. 4 shows the average enumeration of yeast in dark chocolate sauce with different preservative treatments over time with error bars depicting the standard deviation of the mean.

The yeast levels in the dark chocolate sauce immediately after challenging ranged from $1.7 \times 10^3$ to $2.0 \times 10^3$ CFU/g (Table 12, FIG. 4) indicating that the challenge dose was consistent between treatments. The yeast levels in all treatments began to decrease over the first 35 days, however, at a different rate for each treatment (FIG. 4). The dark chocolate sauce treated with either of the *L. reuteri* fermentate treatments followed a similar trend with a rapid decrease in yeast through day 18 at which point the levels were no longer detectable (<10 CFU/g). The Potassium sorbate and Propionic acid-based fermentate treatments decreased yeast levels at a slower rate with levels becoming undetectable at day 35. Both of the Potassium sorbate and Propionic acid-based fermentate treatments had a resurgence of yeast in the dark chocolate sauce starting at day 49 which decreased by day 63 and then resurfaced again at day 94 with more pronounced yeast levels and continued through day 124. Both of the *L. reuteri* fermentate treatments had yeast levels in the dark chocolate sauce remain undetectable from day 18 through the end of the study.

Figure 5:
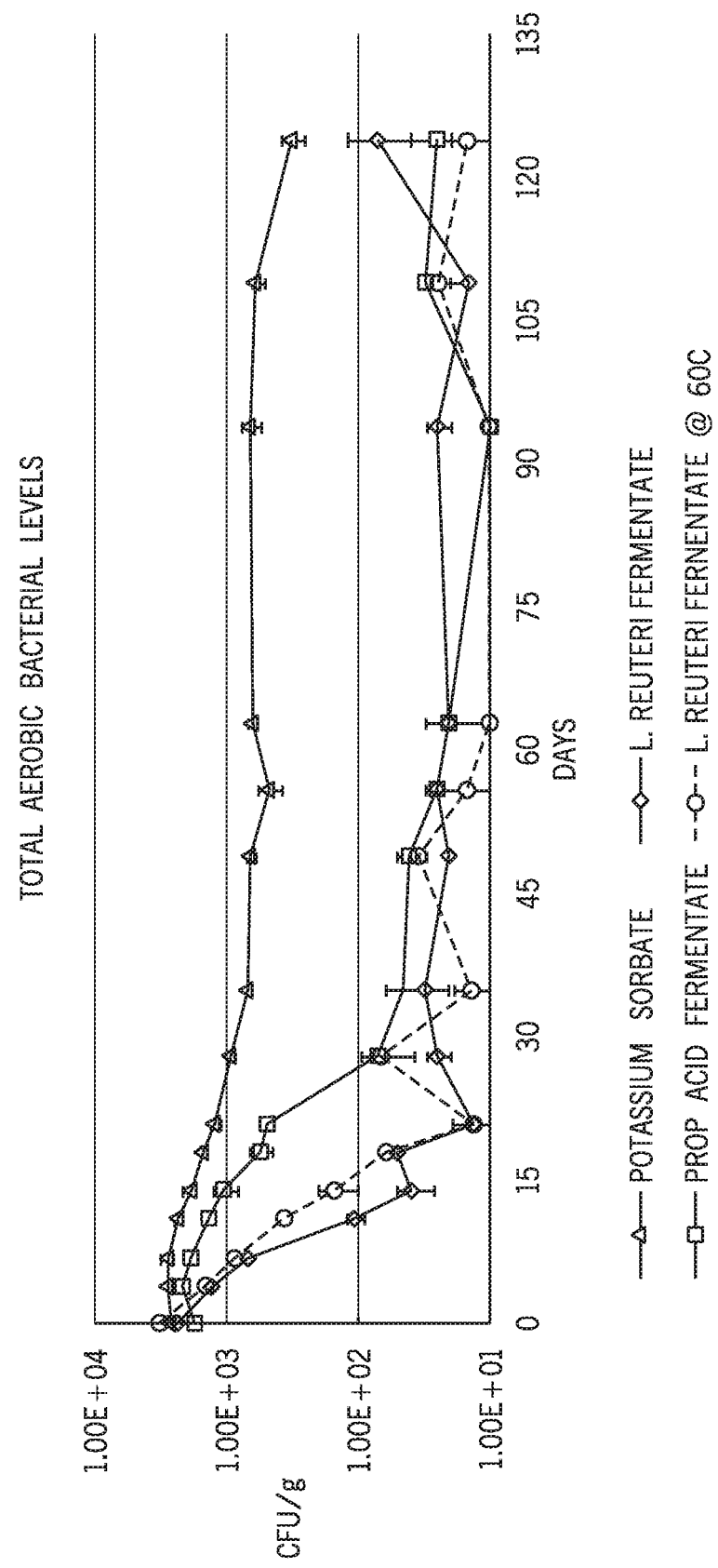
FIG. 5 shows the average enumeration of APC in dark chocolate sauce with different preservative treatments over time with error bars depicting the standard deviation of the mean.

The aerobic plate count (APC) levels in the dark chocolate sauce immediately after challenging ranged from 1.7) ($10^3$ to $3.1 \times 10^3$ CFU/g (Table 13, FIG. 5). The APC levels in the chocolate sauce treated with either of the *L. reuteri* fermentate treatments had a similar decrease with a rapid drop by day 21 and stayed below $1.0 \times 10^2$ CFU/g through day 124. The APC levels in the chocolate sauce treated with the Propionic acid-based fermentate decreased at a slower rate than the *L. reuteri* fermentate treated sauces but dropped below $1.0 \times 10^2$ CFU/g by day 28 and remained below this level through day 124. The dark chocolate sauce treated with Potassium sorbate had APC levels decrease but was not able to lower levels below $3.0)(10^2$ CFU/g through the end of the study.

TABLE 12

Enumeration of yeast in dark chocolate sauce with different preservative treatments over time with duplicate counts listed as colony forming units per gram (CFU/g), averages, and standard deviation.

| | Potassium Sorbate | | | | Propionic Acid Fermentate | | | |
|---|---|---|---|---|---|---|---|---|
| Days | CFU/g | | AVG | STDEV | CFU/g | | AVG | STDEV |
| 0 | 1.73E+03 | 2.27E+03 | 2.00E+03 | 268.8 | 1.81E+03 | 1.84E+03 | 1.83E+03 | 15.0 |
| 4 | 9.49E+02 | 1.51E+03 | 1.23E+03 | 281.6 | 1.34E+03 | 7.10E+02 | 1.03E+03 | 315.0 |
| 7 | 6.43E+02 | 1.17E+03 | 9.08E+02 | 264.9 | 4.92E+02 | 9.94E+02 | 7.43E+02 | 251.0 |
| 11 | 1.10E+03 | 9.43E+02 | 1.02E+03 | 80.2 | 4.61E+02 | 7.62E+02 | 6.12E+02 | 150.5 |
| 14 | 4.99E+02 | 5.98E+02 | 5.48E-02 | 49.9 | 1.66E+02 | 4.50E+02 | 3.08E+02 | 141.8 |
| 18 | 1.40E+02 | 5.19E+02 | 3.30E+02 | 189.8 | 1.01E+01 | 6.09E+01 | 3.55E+01 | 25.4 |
| 21 | 1.17E+02 | 2.94E+02 | 2.06E+02 | 88.1 | 1.22E+02 | 6.10E+01 | 9.15E+01 | 30.5 |
| 28 | 1.51E+02 | 1.00E+02 | 1.26E+02 | 25.1 | 2.00E+01 | 1.00E+01 | 1.50E+01 | 5.0 |
| 35 | <10 | <10 | <10 | 0.0 | <10 | <10 | <10 | 0.0 |
| 49 | 2.05E+01 | 1..02E+01 | 1.53E+01 | 5.1 | 6.06E+02 | 7.07E+02 | 6.57E+02 | 50.5 |
| 56 | <10 | <10 | <10 | 0.0 | 3.02E+01 | <10 | 1.56E+01 | 14.6 |
| 63 | <10 | <10 | <10 | 0.0 | <10 | 2.04E+01 | 1.07E+01 | 9.7 |
| 94 | 3.07E+02 | 4.35E+02 | 3.71E+02 | 64.3 | 1.05E+05 | 1.18E+05 | 1.12E+05 | 6800.0 |
| 109 | 4.68E+01 | 2.53E+02 | 1.50E+02 | 102.9 | 1.59E+03 | 8.08E+01 | 8.33E+02 | 752.5 |
| 124 | 1.25E+04 | 1.17E+04 | 1.21E+04 | 400.4 | 8.20E+03 | 9.50E+03 | 8.85E+03 | 650.0 |

| | *L. reuteri* Fermentate | | | | *L. reuteri* Fermenate @ 60° C. | | | |
|---|---|---|---|---|---|---|---|---|
| Days | CFU/g | | AVG | STDEV | CFU/g | | AVG | STDEV |
| 0 | 1.48E+03 | 2.25E+03 | 1.87E+03 | 385.0 | 7.20E+02 | 2.66E+03 | 1.69E+03 | 970.0 |
| 4 | 6.00E+02 | 3.00E+02 | 4.50E+02 | 150.0 | 4.00E+02 | 6.51E+02 | 5.26E+02 | 125.1 |
| 7 | 7.89E+01 | 4.14E+02 | 2.47E+02 | 167.7 | 1.90E+02 | 3.40E+02 | 2.65E+02 | 74.9 |
| 11 | 2.99E+01 | 8.98E+01 | 5.99E+01 | 29.9 | 1.25E+02 | 2.20E+02 | 1.72E+02 | 47.9 |
| 14 | 1.01E+01 | 2.01E+01 | 1.51E+01 | 5.0 | 1.01E+01 | 4.02E+01 | 2.52E+01 | 15.1 |
| 18 | <10 | <10 | <10 | 0.0 | <10 | <10 | <10 | 0.0 |
| 21 | <10 | <10 | <10 | 0.0 | <10 | <10 | <10 | 0.0 |
| 28 | <10 | <10 | <10 | 0.0 | <10 | <10 | <10 | 0.0 |
| 35 | <10 | <10 | <10 | 0.0 | <10 | <10 | <10 | 0.0 |
| 49 | <10 | <10 | <10 | 0.0 | <10 | <10 | <10 | 0.0 |
| 56 | <10 | <10 | <10 | 0.0 | <10 | <10 | <10 | 0.0 |
| 63 | <10 | <10 | <10 | 0.0 | <10 | <10 | <10 | 0.0 |
| 94 | <10 | <10 | <10 | 0.0 | <10 | <10 | <10 | 0.0 |
| 109 | <10 | <10 | <10 | 0.0 | <10 | <10 | <10 | 0.0 |
| 124 | <10 | <10 | <10 | 0.0 | <10 | <10 | <10 | 0.0 |

TABLE 13

Enumeration of APC in dark chocolate sauce with different preservative treatments over time.

| | Potassium Sorbate | | | Propionic Acid Fermentate | | | |
|---|---|---|---|---|---|---|---|
| Days | CFU/g | | AVG | STDEV | CFU/g | | AVG | STDEV |
| 0 | 2.83E+03 | 2.94E+03 | 2.89E+03 | 57.6 | 1.67E+03 | 1.82E+03 | 1.75E+03 | 75.0 |
| 4 | 2.57E+03 | 2.96E+03 | 2.77E+03 | 197.6 | 2.10E+03 | 2.15E+03 | 2.13E+03 | 25.0 |
| 7 | 2.47E+03 | 3.12E+03 | 2.79E+03 | 321.7 | 1.81E+03 | 1.89E+03 | 1.85E+03 | 41.8 |
| 11 | 2.24E+03 | 2.49E+03 | 2.36E+03 | 125.4 | 1.31E+03 | 1.40E+03 | 1.36E+03 | 45.1 |
| 14 | 1.59E+03 | 2.13E+03 | 1.86E+03 | 274.2 | 8.31E+02 | 1.25E+03 | 1.04E+03 | 210.2 |
| 18 | 1.44E+03 | 1.56E+03 | 1.50E+03 | 59.9 | 4.47E+02 | 6.60E+02 | 5.53E+02 | 106.6 |
| 21 | 1.13E+03 | 1.31E+03 | 1.22E+03 | 93.0 | 5.49E+02 | 4.37E+02 | 4.93E+02 | 55.9 |
| 28 | 8.53E+02 | 9.84E+02 | 9.19E+02 | 65.3 | 6.01E+01 | 8.01E+01 | 7.01E+01 | 10.0 |
| 35 | 7.22E+02 | 6.82E+02 | 7.02E+02 | 20.1 | 6.08E+01 | 3.04E+01 | 4.56E+01 | 15.2 |
| 49 | 6.85E+02 | 6.14E+02 | 6.50E+02 | 35.8 | 5.05E+01 | 3.03E+01 | 4.04E+01 | 10.1 |
| 56 | 5.72E+02 | 3.71E+02 | 4.71E+02 | 100.3 | 3.02E+01 | 2.01E+01 | 2.52E+01 | 5.0 |
| 63 | 5.89E+02 | 6.79E+02 | 6.34E+02 | 45.0 | 2.04E+01 | 2.04E+01 | 2.04E+01 | 0.0 |
| 94 | 5.54E+02 | 7.62E+02 | 6.58E+02 | 103.9 | <10 | <10 | <10 | 0.0 |
| 109 | 6.36E+02 | 5.52E+02 | 5.94E+02 | 42.1 | 3.03E+01 | 3.03E+01 | 3.03E+01 | 0.0 |
| 124 | 2.52E+02 | 3.78E+02 | 3.15E+02 | 62.9 | 1.00E+01 | 4.00E+01 | 2.50E+01 | 15.0 |

| | L. reuteri Fermentate | | | | L. reuteri Fermentate @ 60° C. | | | |
|---|---|---|---|---|---|---|---|---|
| Days | CFU/g | | AVG | STDEV | CFU/g | | AVG | STDEV |
| 0 | 2.25E+03 | 2.39E+03 | 2.32E+03 | 70.0 | 2.80E+03 | 3.40E+03 | 3.10E+03 | 300.0 |
| 4 | 1.37E+03 | 1.29E+03 | 1.33E+03 | 40.0 | 1.29E+03 | 1.53E+03 | 1.41E+03 | 120.1 |
| 7 | 6.21E+02 | 7.59E+02 | 6.90E+02 | 69.0 | 7.89E+02 | 9.29E+02 | 8.59E+02 | 69.9 |
| 11 | 8.98E+01 | 1.20E+02 | 1.05E+02 | 15.0 | 3.35E+02 | 3.74E+02 | 3.54E+02 | 19.2 |
| 14 | 3.02E+01 | 5.03E+01 | 4.02E+01 | 10.1 | 1.01E+02 | 2.01E+02 | 1.51E+02 | 50.3 |
| 18 | 4.98E+01 | 4.98E+01 | 4.98E+01 | 0.0 | 5.91E+01 | 5.91E+01 | 5.91E+01 | 0.0 |
| 21 | 1.33E+01 | 1.33E+01 | 1.33E+01 | 0.0 | 1.90E+01 | <10 | 1.43E+01 | 4.8 |
| 28 | 2.00E+01 | 2.99E+01 | 2.50E+01 | 5.0 | 9.46E+01 | 3.78E+01 | 6.62E+01 | 28.4 |
| 35 | 2.02E+01 | 4.04E+01 | 3.03E+01 | 10.1 | 1.89E+01 | 9.44E+00 | 1.42E+01 | 4.7 |
| 49 | 2.03E+01 | 2.03E+01 | 2.03E+01 | 0.0 | 3.93E+01 | 2.95E+01 | 3.44E+01 | 4.9 |
| 56 | 2.00E+01 | 3.00E+01 | 2.50E+01 | 5.0 | <10 | 1.96E+01 | 1.47E+01 | 4.9 |
| 63 | 1.02E+01 | 3.06E+01 | 2.04E+01 | 10.2 | <10 | <10 | <10 | 0.0 |
| 94 | 1.98E+01 | 2.97E+01 | 2.48E+01 | 5.0 | <10 | <10 | <10 | 0.0 |
| 109 | 2.90E+01 | <10 | 1.45E+01 | 14.5 | 1.92E+01 | 2.89E+01 | 2.40E+01 | 4.8 |
| 124 | 1.21E+01 | 2.01E+01 | 7.04E+01 | 50.3 | <10 | 1.97E+01 | 1.48E+01 | 4.9 |

Example 12—Fermentation of *Lactobacillus reuteri* can Reduce Yeast Challenge in Green Tea and Maintain Activity During High Heat and Pressure Green Tea (Bigelow Classic) was prepared by adding four tea bags to 900 ml boiling hot distilled water and allowed to steep for 5 minutes. Tea was cooled and then 100 ml was transferred to four 250 ml Erlenmeyer flasks with the addition of 0.5 grams (0.5%) granulated white sugar to each. Two of the flasks also received 1 gram (1%) of *Lactobacillus reuteri* spray dried fermentate. All flasks were covered with foil and then steam sterilized at 121° C. at 15 psi pressure for 15 minutes.

Once cooled, all four flasks were inoculated with a dual yeast challenge of *Saccharomyces cerevisiae* strain, Y-1545, and *Zygosaccharomyces rouxii* strain, Y-229, which were obtained from the ARS NRRL Culture Collection. Yeast strains were grown in Potato Dextrose broth at 32° C. overnight, then diluted in sterile water to approximately $3.0 \times 10^4$ CFU/ml. The two strains were then combined and 1 ml of the combination culture was added to each flask to provide a challenge dose of approximately $3.0 \times 10^2$ CFU/ml.

A 2 ml sample was removed from each flask after challenge inoculation to analyze the pH and the initial yeast count on Potato Dextrose Agar acidified with 10% Tartaric Acid (PDA+TA) in duplicate. Once solidified, the PDA+TA plates were incubated aerobically at room temperature (~25° C.) for 72 hours. Flasks were incubated at room temperature (~25° C.), in a shaking incubator set at 100 rpm for the duration of the study. On days 1, 4, and 6, a 2 ml sample was removed from each flask to analyze the change in pH and yeast count on PDA+TA in duplicate.

Figure 6:
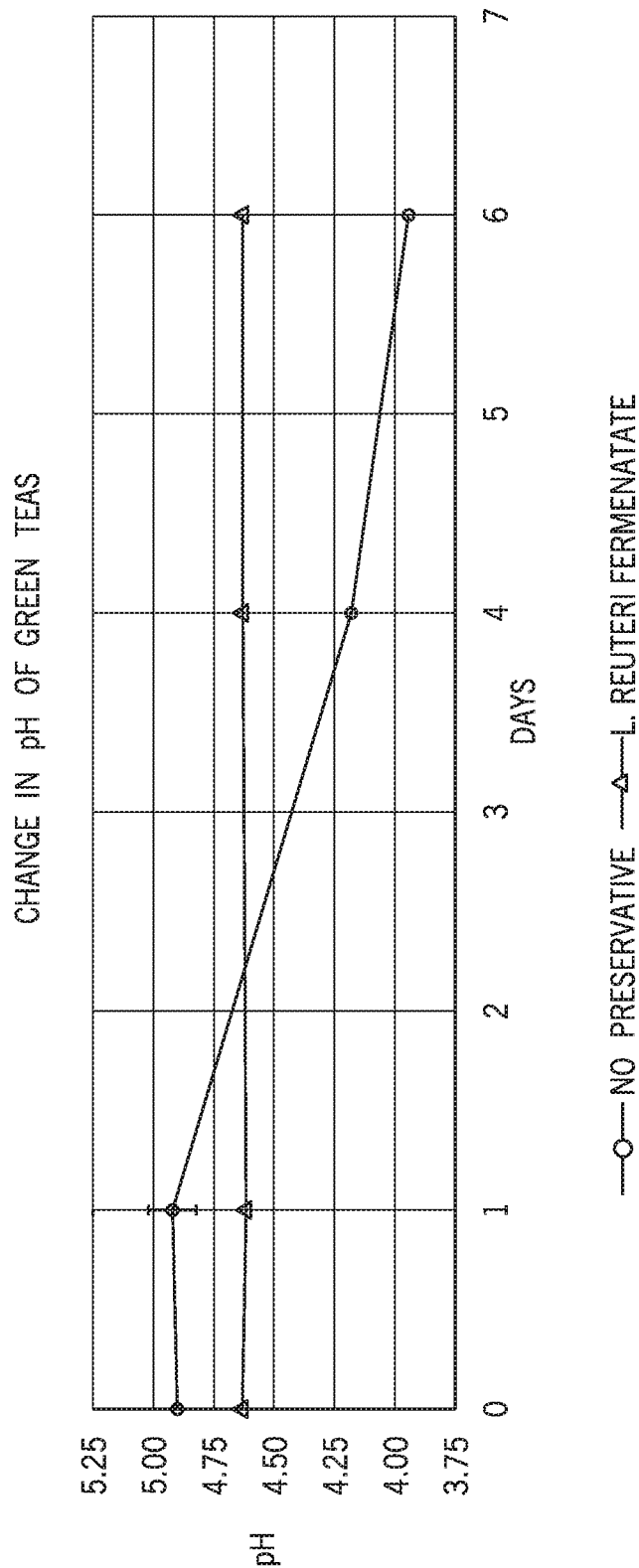
FIG. 6 shows the average change in pH of green tea flasks with and without the addition of *L. reuteri* fermentate over time with error bars depicting the standard deviation of the mean.

Results:

The pH of the green tea in flasks of the same treatment were within 0.1 pH units throughout the analysis except for the No Preservative treated flasks at Day 1 which were 0.24 units different (Table 14, FIG. 6). The pH of the No Preservative treatment initially increased slightly at day 1 and then began to drop by day 4 and continued to drop more drastically by day 6 (FIG. 6). The pH of the *L. reuteri* fermentate flasks held steady from day of challenge, Day 0 through Day 6, with a pH of 4.64 and 4.63 average, respectively.

TABLE 14 pH of green tea flasks with and without addition of *L. reuteri* fermentate over time.

| | No Preservative | | | | *L. reuteri* fermentate | | | |
|---|---|---|---|---|---|---|---|---|
| Days | Flask A | Flask B | AVG | STDEV | Flask A | Flask B | AVG | STDEV |
| 0 | 4.90 | 4.88 | 4.89 | 0.0 | 4.63 | 4.64 | 4.64 | 0.0 |
| 1 | 5.04 | 4.80 | 4.92 | 0.1 | 4.62 | 4.61 | 4.62 | 0.0 |
| 4 | 4.20 | 4.15 | 4.18 | 0.0 | 4.63 | 4.63 | 4.63 | 0.0 |
| 6 | 3.94 | 3.92 | 3.93 | 0.0 | 4.62 | 4.63 | 4.63 | 0.0 |

Figure 7:
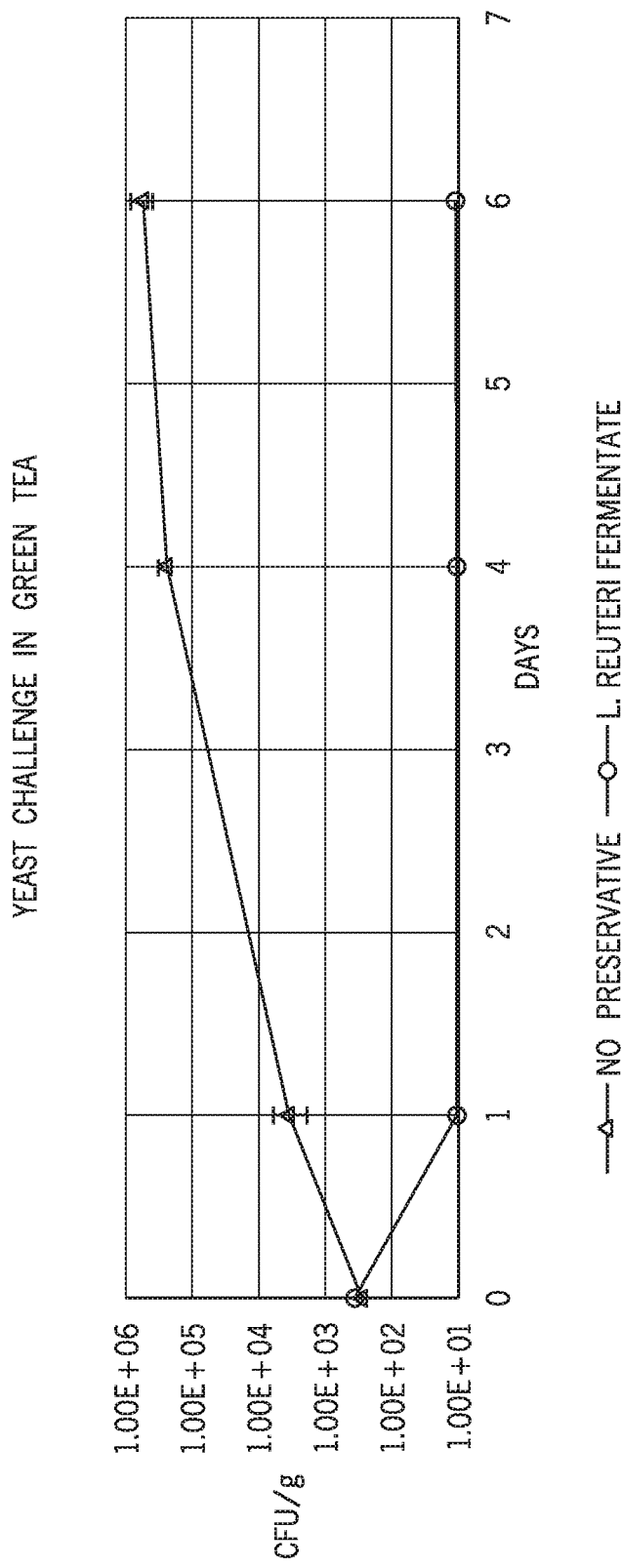
FIG. 7 shows the average enumeration of yeast in green tea flasks with and without the addition of *L. reuteri* fermentate over time with error bars depicting the standard deviation of the mean.

The green tea was sterilized prior to yeast challenge, therefore, only yeast was enumerated from each flask for the duration of the study (Table 15, FIG. 7). On the day of challenge, the flasks with No Preservative had an average of $2.98 \times 10^2$ CFU/ml and the *L. reuteri* treated flasks had an average of $3.35 \times 10^2$ CFU/ml, both of which were within the anticipated challenge dose of $3.0 \times 10^2$ CFU/ml. The yeast levels in the flasks with No Preservative steadily increased at Days 1 and 4, until beginning to level off at Day 6 with an average of $6.03 \times 10^5$ CFU/ml (FIG. 7). The *L. reuteri* treated flasks dropped below detectable limits (<10 CFU/ml) on all days after the initial challenge.

were also analyzed for pH and any changes in visual or sensory observations were recorded.

Results:

Throughout the shelf life of the potato salads, there were little changes in visual appearance. There was no mold present in either salad through week 4 and the PDA+TA media only detected yeast, no mold.

The pH of the potato salad with no preservative started at 5.35 and held steady through week 1 with a gradually

TABLE 15

Enumeration of yeast in green tea over time with duplicate counts listed as colony forming units per ml (CFU/ml), averages, and standard deviation.

| | No Preservative | | | | | |
|---|---|---|---|---|---|---|
| Days | Flask A (CFU/ml) | | Flask B (CFU/ml) | | AVG | STDEV |
| 0 | 2.60E+02 | 3.40E+02 | 2.70E+02 | 3.20E+02 | 2.98E+02 | 33.4 |
| 1 | 5.50E+03 | 5.60E+03 | 2.20E+03 | 1.50E+03 | 3.70E+03 | 1866.8 |
| 4 | 1.90E+05 | 2.10E+05 | 3.10E+05 | 3.30E+05 | 2.60E+05 | 60827.6 |
| 6 | 6.30E+05 | 9.10E+05 | 3.30E+05 | 5.40E+05 | 6.03E+05 | 208251.7 |

| | *L. reuteri* fermentate | | | | | |
|---|---|---|---|---|---|---|
| Days | Flask A (CFU/ml) | | Flask B (CFU/ml) | | AVG | STDEV |
| 0 | 2.40E+02 | 2.70E+02 | 3.20E4+02 | 5.10E+02 | 3.35E+02 | 105.0 |
| 1 | <10 | <10 | <10 | <10 | <10 | — |
| 4 | <10 | <10 | <10 | <10 | <10 | — |
| 6 | <10 | <10 | <10 | <10 | <10 | — |

Example 13—Fermentation of *Lactobacillus reuteri* can Delay Spoilage in Potato Salad A standard creamy style potato salad was prepared using a recipe of cubed potatoes, chopped hard boiled eggs, diced celery and onion, black pepper, onion salt, sugar, mayonnaise, mustard, and fresh parsley. The mayonnaise was prepared with and without the addition of 2% *L. reuteri* spray dried fermentate prior to blending with the salad ingredients. The salads were packaged in 2-pound containers and stored at refrigerated temperature (4-8° C.). A 22-gram sample was removed and tested from each salad weekly for 4 weeks to determine the microbial spoilage of the potato salad over time.

Figure 8:
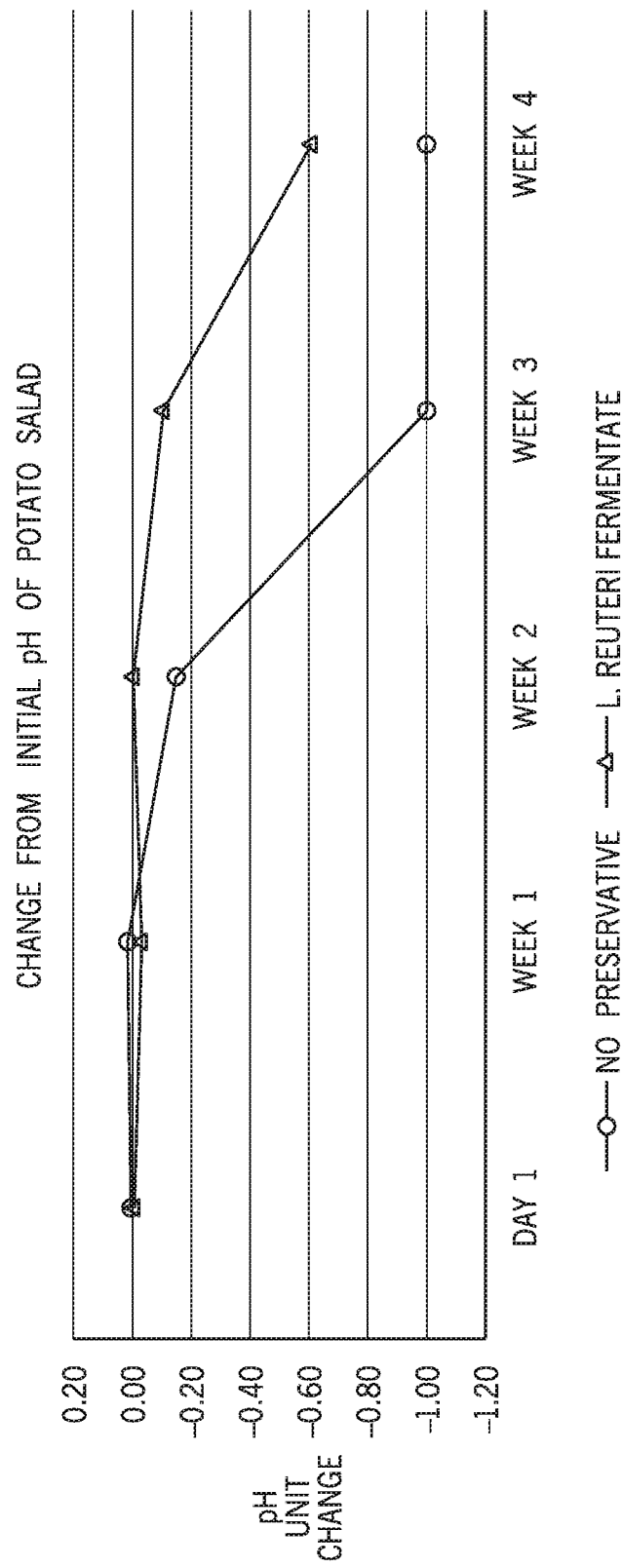
FIG. 8 shows the change in pH of potato salad over time with and without treatment with a *L. reuteri* fermentate.

The samples were diluted with 0.1% sterile buffered peptone water, masticated, and further diluted before enumerating in duplicate on DeMan, Rogosa, Sharpe (MRS) agar for Lactic Acid Bacteria, Tryptic Soy Agar (TSA) for Aerobic Plate Count, and acidified Potato Dextrose Agar with 10% Tartaric Acid (PDA+TA) for Yeast and Molds. The MRS plates were incubated anaerobically at 32° C. for 48 hours, the TSA plates were incubated aerobically at 32° C. for 48 hours, and the PDA+TA plates were incubated aerobically at 28° C. for 72 hours for recovery of yeast and an additional 24-48 hours for recovery of mold. Samples decrease at week 2 and a more dramatic decrease at week 3, at which point the pH leveled off 1 pH unit below the starting point, finishing at 4.34 through week 4 (FIG. 8). The pH of the salad with the *L. reuteri* fermentate started at 5.01 and held steady through week 2 with a slight decrease in pH occurring at week 3 and dropping 0.6 pH units below the starting point at week 4, finishing at 4.40. The salad with the *L. reuteri* fermentate was able to hold the pH steady for one week longer than the salad with no preservative and although had a lower starting pH, finished above the pH of the no preservative salad by week 4.

Figure 9:
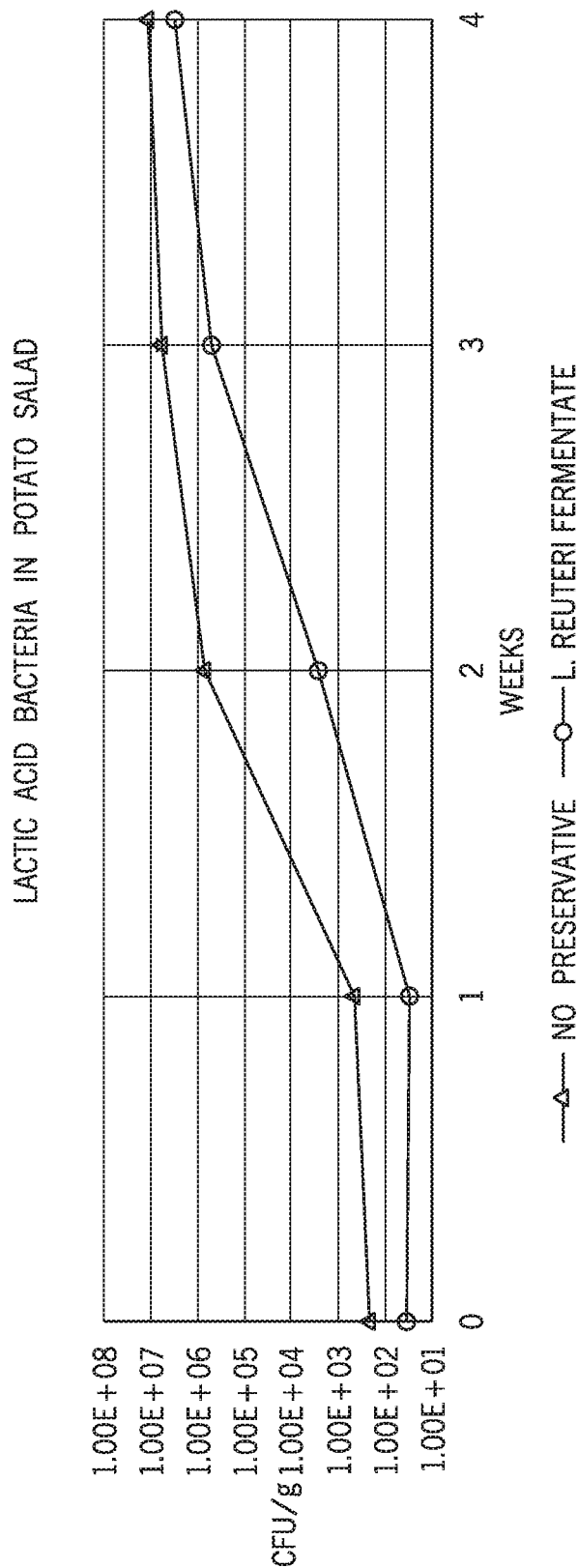
FIG. 9 shows the average of duplicate counts of Lactic Acid Bacteria in potato salad over time with and without treatment with a *L. reuteri* fermentate. Standard deviations are depicted with error bars.

The Lactic Acid Bacteria (LAB) levels in the potato salad with no preservative and *L. reuteri* fermentate had average starting levels of $2.3 \times 10^2$ CFU/g and $3.5 \times 10^1$ CFU/g, respectively (Table 16) and these levels held steady in both salads through week 1 (FIG. 9). By week 2, the salad with no preservative increased 3.5-logs to $7.68 \times 10^5$ CFU/g and the salad with the *L. reuteri* fermentate increased 2-logs to $2.63 \times 10^3$ CFU/g, resulting in a 2.5-log difference in LAB levels. From week 3 to week 4, the salad with no preservative had LAB levels increase from $6 \times 10^6$-$1 \times 10^7$ CFU/g, whereas the salad with the *L. reuteri* fermentate increased in LAB levels at week 4 to $3 \times 10^6$ CFU/g, almost 1-log lower than the salad with no preservative at week 4.

TABLE 16

Lactic Acid Bacteria enumeration in potato salad over time with duplicate counts, averages and standard deviation.

| | No Preservative | | AVG | STDEV | *L. reuteri* fermentate | | AVG | STDEV |
|---|---|---|---|---|---|---|---|---|
| Day 1 | 1.82E+02 | 2.87E+02 | 2.34E+02 | 52.6 | 3.00E+01 | 4.01E+01 | 3.51E+01 | 5.0 |
| Week 1 | 4.81E+20 | 4.42E+02 | 4.62E+02 | 19.7 | 3.00E+01 | 3.00E+01 | 3.00E+01 | 0.0 |
| Week 2 | 7.44E+05 | 7.93E+05 | 7.68E+05 | 24469.1 | 2.53E+03 | 2.72E+03 | 2.63E+03 | 97.3 |

TABLE 16-continued

Lactic Acid Bacteria enumeration in potato salad over time with duplicate counts, averages and standard deviation.

|  | No Preservative | | AVG | STDEV | L. reuteri fermentate | | AVG | STDEV |
|---|---|---|---|---|---|---|---|---|
| Week 3 | 4.20E+06 | 8.20E+06 | 6.20E+06 | 1998989.9 | 4.90E+05 | 5.39E+05 | 5.14E+05 | 24041.7 |
| Week 4 | 1.04E+07 | 1.15E+07 | 1.09E+07 | 543423.0 | 3.15E+06 | 3.05E+06 | 3.10E+06 | 49153.0 |

Figure 10:
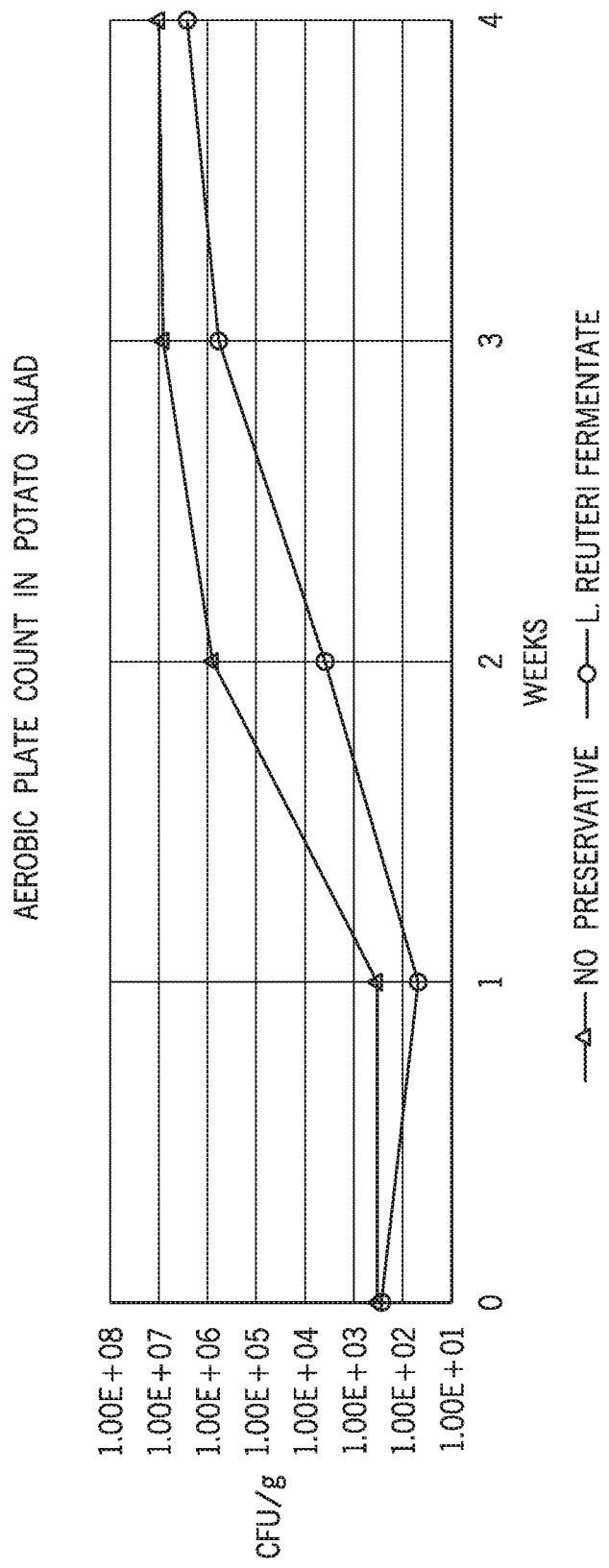
FIG. 10 shows the average of duplicate counts of aerobic plate count in potato salad over time with and without treatment with a *L. reuteri* fermentate. Standard deviations are depicted with error bars.

The Aerobic Plate Count (APC) in the potato salad with no preservative and *L. reuteri* fermentate had starting levels of $3.2 \times 10^2$ CFU/g and $2.6 \times 10^2$ CFU/g, respectively (Table 17). Through week 1, the APC levels held steady in the salad with no preservative and decreased in the salad with *L. reuteri* fermentate (FIG. 10). By week 2, the salad with no preservative increased 2.5-logs to $8.1 \times 10^5$ CFU/g and the salad with the *L. reuteri* fermentate increased 2-logs to $3.8 \times 10^3$ CFU/g, resulting in a 2.5 log difference in APC levels. From week 3 to week 4, the salad with no preservative had APC levels increase from $7 \times 10^6$-$1 \times 10^7$ CFU/g whereas the salad with the *L. reuteri* fermentate increased APC levels to $2.6 \times 10^6$ CFU/g at week 4, approximately 1-log lower than the salad with no preservative at week 4.

TABLE 17

Aerobic Plate Count enumeration in potato salad over time with duplicate counts, averages, and standard deviation.

|  | No Preservative | | AVG | STDEV | L. reuteri fermentate | | AVG | STDEV |
|---|---|---|---|---|---|---|---|---|
| Day 1 | 3.06E+02 | 3.25E+02 | 3.16E+02 | 9.6 | 2.40E+02 | 2.70E+02 | 2.55E+02 | 15.0 |
| Week 1 | 3.54E+02 | 2.55E+02 | 3.05E+02 | 49.1 | 4.00E+01 | 5.00E+01 | 4.50E+01 | 5.0 |
| Week 2 | 7.75E+05 | 8.53E+05 | 8.14E+05 | 38661.2 | 4.08E+03 | 3.60E+03 | 3.84E+03 | 243.1 |
| Week 3 | 6.70E+06 | 8.60E+06 | 7.65E+06 | 949520.2 | 5.19E+05 | 5.96E+05 | 5.58E+05 | 38466.8 |
| Week 4 | 9.88E+06 | 1.04E+07 | 1.01E+07 | 247010.5 | 2.49E+06 | 2.61E+06 | 2.55E+06 | 63898.9 |

Figure 11:
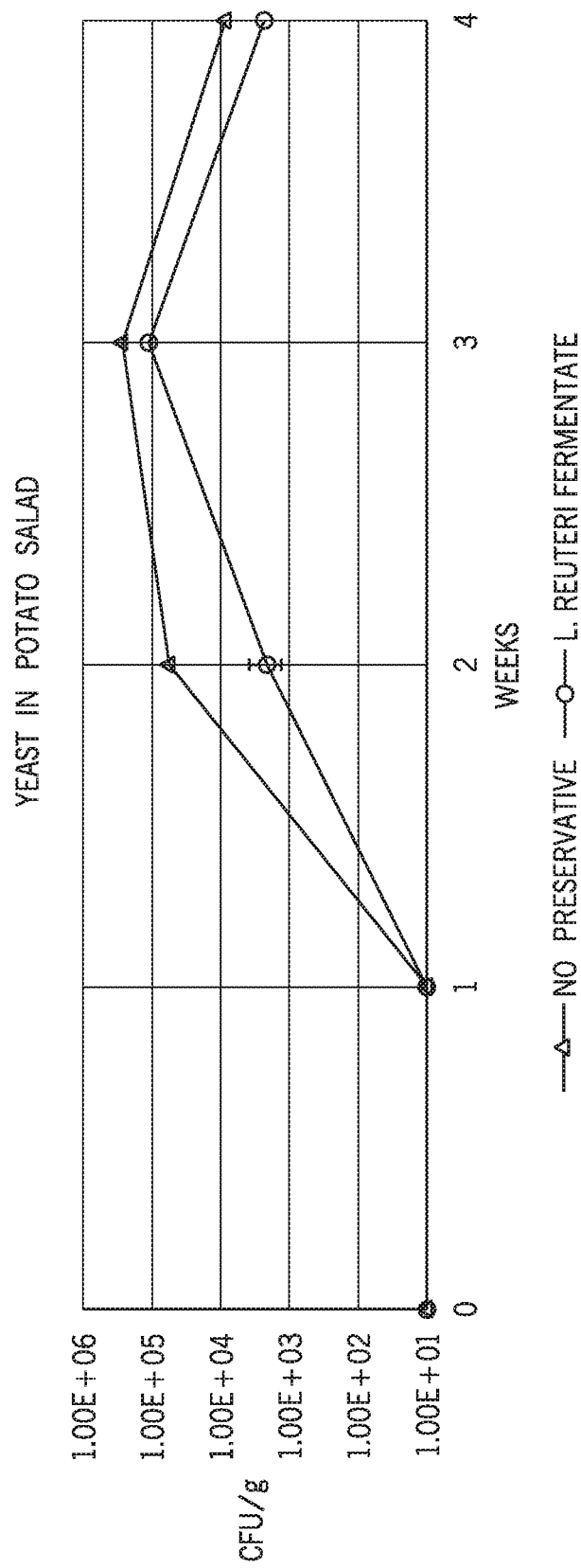
FIG. 11 shows the average of duplicate counts of yeast and mold in potato salad over time with and without treatment with a L. reuteri fermentate. Standard deviations are depicted with error bars.

The yeast counts in the potato salad with no preservative and *L. reuteri* fermentate had undetectable levels (<10 CFU/g) through week 1 (Table 18). Beginning at week 2, yeast was detected in both salads with a 4.5-log increase in the no preservative salad to $6 \times 10^4$ CFU/g and a 3-log increase in the *L. reuteri* fermentate salad to $2 \times 10^3$ CFU/g (FIG. 11). By week 3, both salads had yeast levels within a half log of each other with counts>$1 \times 10^5$ CFU/g but they both dropped in levels at week 4 with the no preservative salad at $9 \times 10^3$ CFU/g and the salad with the *L. reuteri* fermentate over a half-log lower at $2 \times 10^3$ CFU/g yeast.

TABLE 18

Yeast enumeration in potato salad over time with duplicate counts, averages, and standard deviation.

|  | No Preservative | | AVG | STDEV | L. reuteri fermentate | | AVG | STDEV |
|---|---|---|---|---|---|---|---|---|
| Day 1 | <10 | <10 | <10 | 0.0 | <10 | <10 | <10 | 0.0 |
| Week 1 | <10 | <10 | <10 | 0.0 | <10 | <10 | <10 | 0.0 |
| Week 2 | 5.27E+04 | 6.87E+04 | 6.07E+04 | 8025.9 | 9.63E+02 | 3.20E+03 | 2.08E+03 | 1118.5 |
| Week 3 | 2.40E+05 | 2.80E+05 | 2.60E+05 | 19989.9 | 9.42E+04 | 1.28E+05 | 1.11E+05 | 16829.2 |
| Week 4 | 9.88E+03 | 7.90E+03 | 8.89E+03 | 988.0 | 3.44E+03 | 8.85E+02 | 2.16E+03 | 1278.0 |

We claim:

1. A method for inhibiting the growth of a contaminating microorganism on a food product susceptible to microbial contamination or degradation comprising:
   making or obtaining a fermentate comprising reuterin (β-hydroxypropionaldehyde) at a purity between about 0.1% and 40%; and
   applying the fermentate in an amount between about 0.1% and about 5% by weight of a food product to at least one surface of the food product so as to inhibit the growth of the contaminating microorganism on the food product.

2. The method of claim 1, wherein the reuterin is at a purity between about 1% and about 20% in the fermentate.

3. The method of any one of claim 1, wherein the fermentate is applied in an amount between about 1-fold to 20-fold compared to a negative control.

4. The method of claim 1, wherein the fermentate is a *Lactobacillus reuteri* fermentate.

5. The method of claim 1, wherein the food product has a pH between about 3 and about 8.

6. The method of claim 1, wherein the food product has a water activity greater than 0.6.

7. The method of claim 1, wherein the food product is selected from the group consisting of culinary items, bakery items, cereals, pasta, meats, dairy items, rice, fish, nuts, beverages, confections, syrups, pet food, fruits, and vegetables.

8. The method of claim 1, wherein the contaminating microorganism is selected from the group consisting of a yeast species, a mold species, a gram positive bacteria, and a gram negative bacteria.

9. The method of claim 8, wherein the contaminating microorganism is selected from the group consisting of a *Rhodotorula* species, a *Lactobacillus* species, a *Saccharomyces* species, *Zygosaccharomyces* species, a *Candida* species, a *Leuconostoc* species, a *Lactococcus* species, and a *Pedioccocus* species.

10. The method of claim 1, wherein the making or obtaining a fermentate further comprises making or obtaining the fermentate under anaerobic conditions.

11. The method of claim 10, wherein the making or obtaining the fermentate comprises making or obtaining a first liquid composition including a fermentable carbohydrate, *Lactobacillus reuteri*, water, and a growth media and sparging nitrogen gas through the liquid composition.

12. The method of claim 10, wherein the making or obtaining the fermentate under anaerobic conditions comprises making or obtaining a first liquid composition including a fermentable carbohydrate, *Lactobacillus reuteri*, water, and a growth media in a fermentation vessel having a headspace, and setting nitrogen gas over the headspace of the fermentation vessel.

13. The method of claim 1 further comprising spray drying the fermentate before applying the fermentate.

\* \* \* \* \*